US010598600B2

United States Patent
Bremer et al.

(10) Patent No.: US 10,598,600 B2
(45) Date of Patent: Mar. 24, 2020

(54) OPTICAL SENSOR SYSTEM

(71) Applicant: GOTTFRIED WILHELM LEIBNIZ UNIVERSITAT HANNOVER, Hannover (DE)

(72) Inventors: Kort Bremer, Hannover (DE); Bernhard Roth, Bielefeld (DE); Johanna-Gabriela Walter, Nienburg (DE)

(73) Assignee: GOTTFRIED WILHELM LEIBNIZ UNIVERSITAT HANNOVER, Hannover (DE)

( * ) Notice: Subject to any disclaimer, the term of this patent is extended or adjusted under 35 U.S.C. 154(b) by 300 days.

(21) Appl. No.: 15/544,974

(22) PCT Filed: Nov. 4, 2015

(86) PCT No.: PCT/EP2015/075704
§ 371 (c)(1),
(2) Date: Jul. 20, 2017

(87) PCT Pub. No.: WO2016/116181
PCT Pub. Date: Jul. 28, 2016

(65) Prior Publication Data
US 2018/0017495 A1    Jan. 18, 2018

(30) Foreign Application Priority Data
Jan. 21, 2015    (DE) .......... 10 2015 100 845

(51) Int. Cl.
*G01N 21/01* (2006.01)
*G01N 21/78* (2006.01)
(Continued)

(52) U.S. Cl.
CPC ........ *G01N 21/78* (2013.01); *B01L 3/502707* (2013.01); *B01L 3/502761* (2013.01);
(Continued)

(58) Field of Classification Search
CPC ....... B01L 2300/0654; B01L 3/502707; B01L 3/502761; G01N 21/553; G01N 21/7703;
(Continued)

(56) References Cited

U.S. PATENT DOCUMENTS

2006/0292039 A1    12/2006    Iida
2008/0204760 A1*    8/2008    Gollier ............... G01D 5/34
                                                              356/484
(Continued)

FOREIGN PATENT DOCUMENTS

WO    2013/102661 A1    7/2013

OTHER PUBLICATIONS

Souza Filho Carlos A De et al: "Smartphone based, portable optical biosensor utilizing surface plasmon resonance", 2014 IEEE International Instrumentation and Measurement Technology Conference (I2MTC) Proceedings, IEEE, pp. 890-895, May 12, 2014.
(Continued)

*Primary Examiner* — Sunghee Y Gray
(74) *Attorney, Agent, or Firm* — W&C IP

(57) ABSTRACT

The invention relates to an optical sensor system, which is designed to interact with a mobile computer device, which has at least one light source and at least one camera, wherein the sensor system has at least one incoupling interface for coupling light from the light source of the computer device into the sensor system and at least one outcoupling interface for coupling light from the sensor system out to the camera of the computer device, wherein the sensor system has at least one optical light-guiding path, by means of which the outcoupling interface is optically connected to the incoupling interface, wherein at least one sensor designed to modify the light guided by the light-guiding path according to a physical quantity influencing the sensor system from outside is arranged in the light-guiding path, wherein at least
(Continued)

Figure 1:
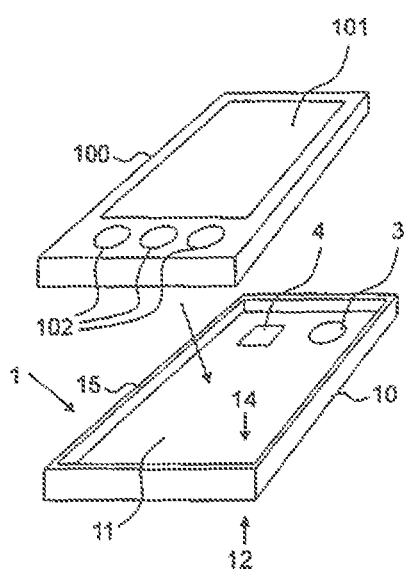

one sensor designed to modify the light guided by the light-guiding path according to an influencing quantity influencing the sensor system from outside is arranged in the light-guiding path, wherein the sensor system has a flatly constructed planar retaining structure, in which the incoupling interface, the outcoupling interface, the elements of the light-guiding path, and the sensor element are structurally integrated and are adjusted in a fixedly specified optical arrangement in relation to each other.

21 Claims, 17 Drawing Sheets

(51) Int. Cl.
*G01N 21/77* (2006.01)
*G01N 21/552* (2014.01)
*B01L 3/00* (2006.01)
*G01N 33/543* (2006.01)

(52) U.S. Cl.
CPC ....... *G01N 21/553* (2013.01); *G01N 21/7703* (2013.01); *G01N 33/54373* (2013.01); *B01L 2300/0654* (2013.01); *G01N 2201/0221* (2013.01)

(58) Field of Classification Search
CPC ........... G01N 21/78; G01N 2201/0221; G01N 33/54373
USPC .................................................. 356/244, 245
See application file for complete search history.

(56) References Cited

U.S. PATENT DOCUMENTS

| | | |
|---|---|---|
| 2009/0103852 A1 | 4/2009 | Hamamoto |
| 2011/0026871 A1 | 2/2011 | Irawan et al. |
| 2011/0207137 A1 | 8/2011 | Malik |
| 2012/0214707 A1* | 8/2012 | Ymeti .................. G01N 21/45 506/9 |
| 2014/0170757 A1 | 6/2014 | Tsai et al. |
| 2014/0273189 A1 | 9/2014 | Ma et al. |
| 2017/0370836 A1* | 12/2017 | Gerion ................. G01N 21/253 |

OTHER PUBLICATIONS

Pakorn Preechaburana et al: "Surface Plasmon Resonance Chemical Sensing on Cell Phones", vol. 51, No. 46, pp. 11753-11756, Nov. 12, 2012.

Kort Bremer et al: "Fibre optic surface plasmon resonance sensor system designed for smartphones", Optics Express, vol. 23, No. 13, pp. 17179-17184, Jun. 23, 2015.

* cited by examiner

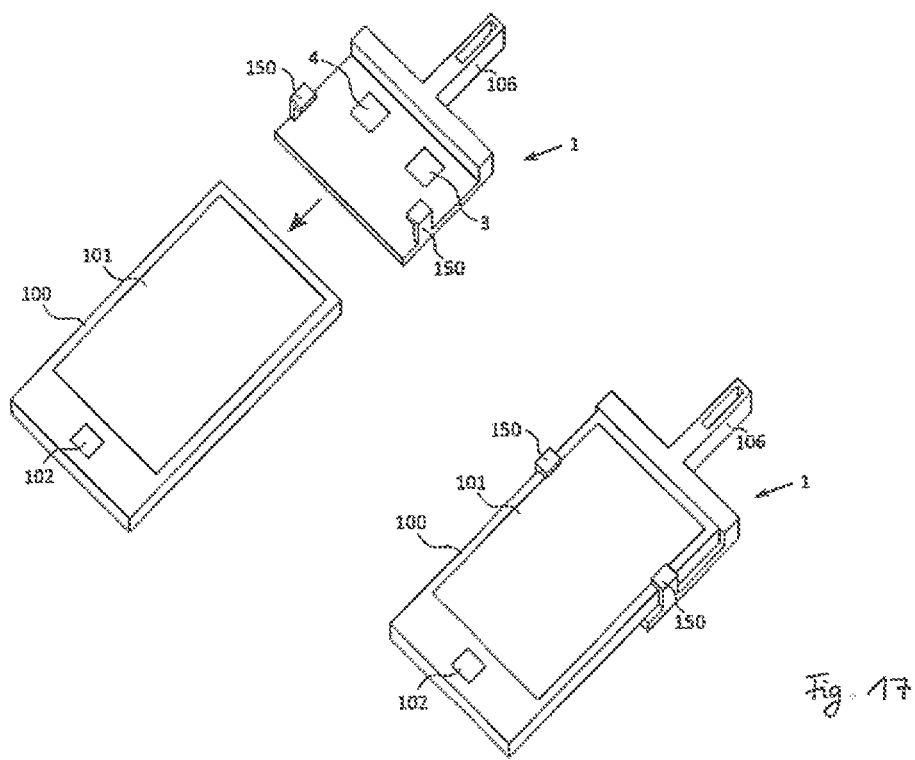

OPTICAL SENSOR SYSTEM

The invention relates to an optical sensor system configured to interact with a mobile computer appliance that comprises at least one light source and at least one camera, wherein the sensor system comprises at least one input coupling interface for the input coupling of light from the light source of the computer appliance into the sensor system and at least one output coupling interface for the output coupling of light from the sensor system to the camera of the computer appliance, wherein the sensor system comprises at least one optical light guiding path, by means of which the output coupling interface is optically connected to the input coupling interface, wherein at least one sensor element is arranged in the light guiding path, said sensor element being configured to modify the light guided through the light guiding path depending on an influencing variable that acts on the sensor system from externally.

WO 2014/107364 A1 describes a smartphone biosensor. Here, a smartphone is extended by appropriate external optical elements to recognize results of a biomolecular assay. However, the structure required to this end is relatively complicated, large and sensitive.

The invention is therefore based on the object of specifying an optical sensor system that is configured for interaction with a mobile computer appliance and that has improved suitability in practice.

In accordance with claim 1, this object is achieved by an optical sensor system configured to interact with a mobile computer appliance that comprises at least one light source and at least one camera, wherein the sensor system comprises at least one input coupling interface for the input coupling of light from the light source of the computer appliance into the sensor system and at least one output coupling interface for the output coupling of light from the sensor system to the camera of the computer appliance, wherein the sensor system comprises at least one optical light guiding path, by means of which the output coupling interface is optically connected to the input coupling interface, wherein at least one sensor element is arranged in the light guiding path, said sensor element being configured to modify the light guided through the light guiding path depending on an influencing variable that acts on the sensor system from externally, wherein the sensor system comprises a flatly constructed plane holding structure into which the input coupling interface, the output coupling interface, the elements of the light guiding path and the sensor element are structurally integrated and adjusted in relation to one another in a fixedly predetermined optical arrangement, An advantage of the invention is that the optical sensor system can be handled in a much more user-friendly manner together with the mobile computer appliance and can be carried along more easily by the user on account of the compact, plane structure. By way of example, if a smartphone is used as a mobile computer appliance, it substantially keeps its external dimensions, even if complemented by the optical sensor system, because the sensor system can be provided in such a compact manner that it hardly adds thickness.

A further advantage of the invention is that the holding structure ensures a defined position of the individual elements integrated therein in particular the input coupling interface, the output coupling interface, the elements of the light guiding path and the sensor element, which are kept in a fixedly predetermined optical arrangement in relation to one another. Accordingly, there are no losses of adjustment between these elements.

As mentioned, the mobile computer appliance can be a smartphone, or any other cellular telephone or a mobile computer appliance of any other type, such as e.g. a laptop, tablet, portable media player (e.g. iPod), smart watch or the like.

The influencing variable acting on the sensor system from externally may be a physical, chemical and/or biochemical variable. One, several or all of the elements structurally integrated into the plane holding structure can be fastened to the plane holding structure, in particular in a detachable manner, in such a way that they can be replaced if necessary. Thus, for example, the sensor element can be embodied as a disposable sensor which can be replaced. Here, the holding structure and/or the remaining elements may be reusable.

In particular, the sensor element arranged in the light guiding path can be an optical sensor. The, optical sensor serves to capture ambient parameters. Ambient parameters can be examined with the aid of e.g. absorption measurements, stray light measurements, reflection light measurements, transmission light measurements, fluorescence light measurements, polarization light measurements, refractive Index measurements, quantum dots and/or the determination of the amplitude spectrum or phase spectrum of the light. The optical sensor can be realized e.g. by means of plasmons, a cavity, an optical evanescence field, an optical grating, photonic crystals, ring resonators or a Fabry-Perot or Mach-Zehnder interferometer or as an optode. Plasmon sensors may be realized, for example, by a gold coating, silver coating and/or by nanostructuring (e.g. nanoparticles). In the case of nano article-based plasmon sensors, the nanoparticles may already be present on the sensor surface before, the application of the sensor system or only be applied onto the sensor surface during the application of the sensor system. Furthermore, use can be made of an adhesive layer between the sensor and metal coating and a grating structure for adapting the phase can be integrated. A plurality of optical sensors can be multiplexed in series and/or in parallel along the optical waveguide, wherein wavelength multiplexing may be applied. Furthermore, it is possible to use lenses for increasing the coupling efficiency of the input and/or output coupling interface.

In particular, the sensor system can be embodied as a lab-on-a-chip.

The input coupling interface can comprise at least one input coupling member, for example in the form of one or more input coupling components. Accordingly, the output coupling interface can contain at least one output coupling member, for example in the form of one or more output coupling components. An input coupling component and/or an output coupling component can be realized by Fresnel reflection/total internal reflection and/or light diffraction. Input coupling components and/or output coupling components may be e.g. optical elements such as mirrors, prisms, angled optical waveguides, optical gratings. Furthermore, nanoparticles may be used for optical coupling purposes.

The efficiency of the input coupling member and/or of the output coupling member can be optimized by means of a lens system and/or a taper structure. Furthermore, the light polarization can be set and optimized by means of a polarization filter as an extension to the input coupling component and/or output coupling component. Moreover, light with a wavelength can be input coupled in a targeted manner by an optical grating as an input coupling member or by changing the color of the display at the location of the input coupler.

The plane holding structure can be formed from rigid or relatively flexible material. In particular, the plane holding structure can be flexible and, in the process, keep its flatly constructed, plane property. The plane holding structure may consist of plastic, metal, natural materials such as wood or cork, of textile material or a combination thereof.

As a result of this, the: sensor system can be produced in a cost-effective manner. On account of the cost-effective production, the sensor system may also be provided as a disposable sensor system. This is advantageous, in particular, when used in cases with high demands on hygiene.

By way of example, the light sour be of the mobile computer appliance can be a light source for illuminating the region captured by the camera of the computer appliance, for example in the form of a flashlight (white light source), an LED (light-emitting diode) or a similar component. By way of example, the light source can also be a display of the mobile computer appliance. In particular, the light source can be embodied as a multi-color light source. This is advantageous in that different wavelengths can be fed into the light guiding path in a targeted manner. The wavelength can be modified at all times by way of appropriate software control, and so specific measurements are only rendered possible hereby. The camera of the mobile computer appliance can be a front-side camera, a rear-side camera or a camera that is arranged on the side.

In accordance with an advantageous development of the invention, the optical sensor system only comprises purely passive components, i.e. those components that do not require an electrical power supply. This is advantageous in that the optical sensor system can be realized without dedicated electrical power source, which is additionally conducive to a compact, cost-effective and simple embodiment of the sensor system. Moreover, replacing or recharging the electrical power supply components is dispensed with.

In accordance with an advantageous development of the invention, the plane holding structure is embodied as a thin, flat structure with two main surfaces facing away from one another, said main surfaces being the outer surfaces of the holding structure with the greatest area, wherein the main surfaces extend substantially parallel to one another. As a result of this, the sensor system can have a particularly compact design such that it does not substantially protrude beyond the mobile computer appliance connected therewith.

In accordance with an advantageous development of the invention, the plane holding structure has a thickness that is substantially less than its width and length. As a result of this, too, the sensor system can have a particularly compact design such that it does not substantially protrude beyond the mobile computer appliance connected therewith.

In particular, it is advantageous to embody the plane holding structure with a thickness that is no greater than the thickness of the mobile computer appliance, with which the optical sensor system is intended to interact.

In accordance with an advantageous development of the invention, the light guiding path that is integrated into the plane holding structure is embodied for substantially parallel light guidance along the main surfaces of the plane holding structure. This allows good use to be made of the available installation space in the holding structure which, per se, has a relatively thin embodiment.

In accordance with an advantageous development of the invention, the light guiding path comprises at least one optical waveguide fitted into the plane holding structure. By way of example, the optical waveguide can be embodied as an optical fiber light guide or a similar light guide, in particular as a flexible light guide. The optical waveguide can be composed of a core and cladding, with the core being optically more dense. The optical waveguide can be embodied as a slab waveguide, ridge waveguide, buried waveguide or fiber waveguide and be single mode or multimode. Furthermore, e.g. the cross-sectional geometry of the optical waveguide can be circular or rectangular, wherein the core and cladding of the optical waveguide may, for example, consist of polymer, glass, silicon or air.

In accordance with an advantageous development of the invention, the light guiding path comprises at least one optical waveguide fitted along an arc, i.e. arcuate optical waveguide, in the plane holding structure. In this way, the light can be guided back from a light source of the computer appliance to the camera of the computer appliance by one and the same optical waveguide, even if said two elements of the computer appliance are arranged closely together.

In accordance with an advantageous development of the invention, the light guiding path comprises at least an input coupling member for the input coupling of the light into the light guiding path at the input coupling interface and/or an output coupling member for the output coupling of the light from the light guiding path at the output coupling interface, wherein the input coupling member and/or the output coupling member is/are configured to at least partly deflect into a direction of longitudinal extent of the light guiding path the light that was input coupled or output coupled in a direction perpendicular to the main surface. In this way, the light emission direction, which, as a rule, is directed perpendicular to a main surface, of the light source of a mobile computer appliance and/or the capture direction, which is directed perpendicular to a main surface, of the camera of a mobile computer appliance, can be adapted with little outlay to the light guiding path that extends substantially parallel to the main surface.

In accordance with an advantageous development of the invention, the plane holding structure comprises at least one mechanical fixation means which assists the correct arrangement and adjustment of the computer appliance relative to the sensor system. The fixation means or the number of fixation means, which, in particular, can be embodied as adjustment means, can be embodied for affixing the computer appliance to the sensor system by force fit (frictional engagement) or form fit, for example in the form of latching means, as clamping connection or as adhesive connection. This is advantageous in that the assembling process between the computer appliance and the optical sensor system is assisted by the fixation means or the number of fixation means and hence simplified for the user. Hence, maladjustments are automatically avoided to the greatest possible extent. The mechanical fixation means can comprise a spring-loaded clamping system, e.g. similar to a clothespin, by means of which the plane holding structure can be clamped onto the computer appliance.

In accordance with an advantageous development of the invention, the sensor system is integrated into, or embodied as, a protective cover of the computer appliance, a piece of clothing or packaging. In this way, the sensor system can be carried along in a particularly inconspicuous manner and is therefore not perceived as bothersome by the user.

In accordance with an advantageous development of the invention, the optical waveguide has an integral embodiment with at least one part of the plane holding structure. In this way, the optical waveguide can be integrated into the holding structure in a particularly expedient manner from a manufacturing point of view.

In accordance with an advantageous development of the invention, the sensor system comprises a plurality of sensors that are arranged in succession in the same light guiding path. In this way, a plurality of sensor signals can be captured and different influencing variables can be sensed by way of one light guiding path. The plurality of sensors that are arranged in succession can then queried during multiplex operation. As a result, it is possible to avoid an extension of the computer appliance to have additional light sources and/or cameras.

In accordance with an advantageous development of the invention, the sensor system comprises a plurality of parallel light guiding paths with at least one sensor element arranged in each light guiding path. In this way, it is also possible to capture a plurality of sensor signals and sense different influencing variables if the computer appliance is equipped with appropriate hardware. Even without a waveguide coupler, a plurality of waveguides can be operated in parallel with an LED and camera.

As a result of multiplexing a plurality of optical sensors, it is possible, for example, to measure a multiplicity of parameters and/or compensate cross sensitivities of the optical sensor structure, for example in relation to temperature. The compensation of cross sensitivities, e.g. temperature and humidity, can also be realized by way of sensors already present in the computer appliance.

For the purposes of functionalizing the sensor region, it is possible, in principle, to immobilize various receptors which specifically bind to the analyte to be detected in the sensor region. Here, it is possible to use both molecules of natural origin, such as e.g. antibodies and enzymes, and synthetically produced molecules, such as e.g. aptamers, as receptors. In addition to the listed macromolecules, it is also possible to immobilize low-molecular molecules on the sensor surface in order to bring about the desired specificity in relation to the analyte to be detected. The immobilization of these receptors on the sensor can be carried out in both covalent and absorptive manner onto the surface of the sensor.

In accordance with an advantageous embodiment of the invention, provision is made for the sensor element to comprise at least one sensor region, on which, as receptors for sensing an analyte to be detected, aptamers or other specificity-imparting receptors, such as e.g. antibodies, which specifically bind to the analyte to be detected, are arranged. In this way, an effective, easy to apply functionalization of the sensor region, e.g. in the form of a sensor surface, is possible. The aptamers or other specificity-imparting receptors such as e.g. antibodies have a high selectivity for detecting specific analytes; therefore, they are particularly suitable for recognizing specific illnesses. In relation to other possible receptors, the aptamers are advantageous in that they are more, stable end therefore permanently functional. The aptamers arranged on the sensor surface or other specificity-imparting receptors such as e.g. antibodies bind the analyte to be detected and, in the process, lead to a change in the optical properties of the medium situated over the sensor surface.

In accordance with an advantageous development of the invention, provision is made of additionally using aptamers or other specificity-imparting receptors such as e.g. antibodies for signal amplification. To this end, use can be made of various modifications which are able to influence the optical properties of the medium over the sensor surface, such as e.g. nanoparticles or dyes. As a result thereof, a further option for amplifying the signal is provided, said option being particularly suitable for relatively large analytes such as proteins or cells. In one possible embodiment, the aptamers or other specificity-imparting receptors such as e.g. antibodies are modified with gold nanoparticles in the process. These modified receptors bind to the analyte which was bound by the aptamers present on the sensor surface or by any other specificity) imparting receptors such as e.g. antibodies. As a result, the modification (e.g. gold nanoparticles) is positioned in the vicinity of the sensor surface and can therefore be used for signal generation and/or signal amplification.

In accordance with an advantageous development of the invention, the sensor element is configured to sense a gas or gas mixture. By way of example, this can be realized by virtue of the sensor element, which is e.g. based on a surface plasmon (SPR) sensor, being functionalized by a (doped or undoped) metal oxide layer or by (doped or undoped) metal oxide layers. Sensors for detecting hydrogen sulfide ($H_2S$), carbon monoxide (CO) or carbon dioxide ($CO_2$), or for ascertaining the air quality, can be realized with the aid of e,g. zinc oxide (ZnO), iron-doped tin dioxide ($Fe:SnO_2$) or zirconium dioxide ($ZrO_2$). Moreover, the specificity in relation to a gas can be improved by the serial/parallel multiplexing of a plurality of sensors with different metal oxide layers or a plurality of different gases can be detected by e.g. a smartphone assisted sensor system.

For the purposes of sensing a gas or gas mixture, the sensor element may, furthermore, be coated by a color-changing material or the waveguide core of the sensor element may be wholly or partly composed of the color-changing material. The color changing material consists of a polymer/dye matrix and color changes of the color-changing material correlate to changes in the gas concentration. On the basis of such a colorimetric method, it is possible to detect gases such as carbon monoxide, nitrogen dioxide, amnonia and/or ethylene.

In accordance with an advantageous development of the invention, the sensor system can be configured to detect spectral properties of the received light. This is advantageous, particularly if the sensor element is embodied as an SPR sensor. The spectral properties and/or the sensitivity of the SPR-based sensor system can be optimized, for example by the core refractive index and/or cladding refractive index of the optical waveguide, by a metal alloy (e.g. silver/gold), by tapering the SPR sensor element, by a dielectric intermediate layer between the SPR sensor element and the ambient medium (functionalization), by a stack (stack of at least two dielectric layers) of different dielectric intermediate layers and/or two metal layers, which are separated by a stank of dielectric intermediate layers.

Moreover, the spectral properties and/or the sensitivity of the SPR-based sensor system (optical waveguide with metal coating) can be optimized by the use of nanoparticles, in particular metal nanoparticles.

In accordance with an advantageous development of the invention, the sensor element can be realized with the aid of Bloch surface waves, for example by virtue of the sensor element being produced by means of a stack of dielectric layers. The metallization of the sensor region and, in particular, of the sensor surface and/or the application of dielectric layers can e.g. be brought about by wet chemical means and/or by means of sputtering and/or electrode beam evaporation.

In accordance with an advantageous development the invention, provision is made for the sensor system to comprise a Fourier transform spectrometer for detecting the light that was modified by the sensor element. This is advantageous in that a reliable detection of the spectrum of the light recorded by the camera can be analyzed. The Fourier transform spectrometer (FT spectrometer) can be used in the sensor system in addition to, or in place of, a diffraction grating. The FT spectrometer is composed of an interferometer which is placed between the sensor system and the smartphone camera The interferogram from the interferometer is recorded by the camera of the computer appliance. It is possible to ascertain the sensor spectrum by calculating the inverse Fourier transform of the interferogram.

In accordance with an advantageous development of the invention, provision is made for the sensor system to have a fluidic or microfluidic system for guiding dissolved analytes toward the sensor element. In this way, the sensor system can be embodied as a lab-on-a-chip, which is also compatible with liquid analytes. The fluidic/microfluidic system serves to guide the sample solution toward the optical sensor element. Furthermore, the lab-on-a-chip can contain buffer solutions which are mixed with the sample solution using the fluidic/microfluidic system and the resultant solution is guided to the optical sensor element by way of the fluidic/microfluidic system. The buffer solution/buffer solutions can moreover be used for sensor regeneration purposes. Furthermore, the buffer solution/buffer solutions integrated on the lab-on-a-chip can be used for calibrating the optical sensor system, said buffer solution/buffer solutions being guided to the optical sensor before the sample solution by means of the fluidic/microfluidic system. Moreover, the smartphone vibration alarm can be used to mix the sample solution and the buffer solution. In addition to the option of the lab-on-a-chip containing solutions, provision can also be made of solids in the, microfluidic system. By way of example, these could be buffer salts, or else other solid reagents, which come into contact with the liquid when the sensor system is applied and, in the process, are transported in dissolved fashion and to the sensor element. This also allows e.g. nanoparticles and/or nanoparticles that are coated with specificity-imparting receptors such as e.g. aptamers or antibodies to be stored in the microfluidic system.

In accordance with an advantageous development of the invention, provision is made for the sensor system to comprise a cavity in the region of the sensor element, said cavity being embodied as an absorption chamber with or without resonator properties. Additionally, the resultant absorption spectrum can be amplified with the aid of metal nanoparticles or fluorescence marks, which are situated in the sample solution and, for example, are able to bind on the targets in a targeted manner.

In accordance with an advantageous development of the invention, provision is made for the plane holding structure to be adjustable in at least one spatial dimension in respect of the effective size of its receiving region for the mobile computer appliance. In this way, it is possible to develop a universally employable sensor system which is suitable for different designs of mobile computer appliances, in particular different smartphones, by virtue of being adaptable to the computer appliance by way of an adjustment.

In accordance with an advantageous development of the invention, provision is made for the sensor system or at least those parts of the sensor system which cover the light source and/or the camera to be adjustable in terms of the position thereof in relation to the holding structure As a result of this, the universal employability of the sensor system in differently embodied mobile computer appliances can be improved further, in particular if different computer appliances have the light source and/or the camera different positions.

In accordance with an advantageous development of the invention, provision is made for the input coupling interface to be composed of a plurality of 45 degree input coupling members that are arranged in series along the tapered/non-tapered optical waveguide such that a uniform, optical sensor system can be used for different mobile computer appliances. Regions of the optical waveguide in which a cross-sectional change, (tapering) of the optical waveguide is present are referred to as being "tapered" or as a taper.

In accordance with an advantageous development of the invention, provision is made for the input coupling interface to be composed of a plurality of parallel 45 degree input coupling members and a tapered optical waveguide, wherein the 45 degree input coupling members may also be arranged with a slight offset such that a uniform optical sensor system can be used for different mobile computer appliances.

In accordance with an advantageous development of the invention, provision is made for the sensor system to be composed of a plurality of parallel optical sensor systems, wherein the lengths of the plurality of parallel optical sensor systems may vary such that the respective input coupling members are situated at different locations and hence such that at least one optical sensor system is always aligned in an ideal manner in relation to the light source and the camera, even if the positions of these components vary depending on the mobile computer appliance.

In accordance with an advantageous development of the invention, provision is made for the input coupling interface and/or output coupling interface to be composed of an optical grating with a chirped grating period. In the region of a chirped grating period, the period changes along the optical path. As a result of this, the suitability of the optical grating for a plurality of wavelengths is improved.

In accordance with an advantageous development of the invention, provision is made for the sensor system to be able to be placed in an arched and/or diagonal (horizontal and/or vertical) manner in order to optimize the optical coupling to the sensor system depending on the smartphone type, (mobile computer appliance). To this end, the sensor system can be of a flexible or bendable embodiment.

In accordance with an advantageous development of the invention, provision is made for the sensor system, or at least those parts of the sensor system which cover the light source and/or the camera to be matched in terms of the size and position thereof to the mobile computer appliance in such a way that the light source and/or the camera is/are only partly covered. In this way, e.g. the light source and/or the camera of the mobile computer appliance may, additionally, still be used for other purposes, e.g. for recording photographs without removing the sensor system. By way of an appropriate image processing software, which may be installed on the mobile computer appliance or any other computer appliance, it is possible to remove from recorded photographs the respective pixel lines and/or pixel columns which are assigned to the sensor system.

Provided that the sensor system is integrated into a smartphone protective cover, the smartphone protective cover can be designed in such a way that the sensor system can be placed flexibly in front of the light source and camera of the smartphone. In this way, the user could flexibly take measurements or photographs using the smartphone. By way of example, a displacement apparatus could be provided in the smartphone protective cover for the flatly constructed sensor structure. Alternatively, the sensor system could be integrated rigidly in the smartphone protective cover and the output coupling member of the sensor system could be designed in such a way that only a few pixel lines or pixel columns of the smartphone camera are required for the sensor evaluation. In a preferred design, said pixel lines or pixel columns are situated at the edge of the smartphone camera, such that, in the case of a conventional photo application, these pixel lines or pixel columns can be deleted from the image.

In accordance with an advantageous development of the invention, the sensor system has at least one 45 degree mirror that is produced by a 45 degree cutting method, a subsequent hot stamping method and/or subsequent material processing in the input coupling interface and/or in the output coupling interface. This allows a reliable and cost-effective production of the sensor system.

The evaluation of the data ascertained by the sensor system or of the image data recorded by the camera of the computer appliance can be carried out directly on the computer appliance itself, or remotely on an external computer. Accordingly, algorithms and software that are appropriate for the evaluation of the data from the sensor system can be executed either directly on the computer appliance or on the external computer. A distributed execution of certain components of the algorithms and software on both appliances, i.e. the mobile computer appliance and the external computer, is also advantageous.

Accordingly, the invention also relates to a computer program to be executed on a computer appliance that interacts with the sensor system of the aforementioned type or on an external computer. In an advantageous embodiment, the computer program is configured to actuate the light source of the computer appliance in a manner modulated with a predetermined modulation scheme and, further, to demodulate the light received by the camera with a demodulation scheme that is assigned to the modulation scheme. By way of example, this can be carried out by a pulsed actuation of the light source, e.g. by means of reliable, error-identifying encoding. In this way, external interference such as stray light can be minimized. Thus, for example, the light source can be switched on and off periodically at an appropriate frequency. As a result of this, it is possible to increase the sensor sensitivity and/or reduce the sensitivity in relation to stray light (ambient light).

In accordance with a further advantageous embodiment, a plurality of measurements can be carried out in sequence and a mean value can be formed, and different measurements can be carried out in sequence.

In accordance with a further advantageous embodiment, the computer appliance is able to instruct or assist the user in relation to the correct application of the sensor system by means of a video that is played back on the computer appliance.

In accordance with a further advantageous embodiment, the computer program can additionally incorporate further data from the mobile computer appliance, such as e.g. a GPS position, for the evaluation of the sensor system. As a result of this, advantageous applications, in the field of travel medicine, can become accessible. Thus, the GPS position can be used, for example, to request urgent medical aid in the spatial vicinity, e.g. by way of an automated emergency call. Further, the GPS position can be used, for example, to additionally make a diagnosis that is established by means of the sensor element more precise, for example by virtue of discounting symptoms that are unlikely for the respective geographic region.

In accordance with a further advantageous embodiment, the computer program is configured to carry out spectral analysis of the signal recorded by the camera. In this way, the sensor element can also be spectrally evaluated directly with the camera of the mobile computer appliance, for example by virtue of the measured intensity values of the camera pixels with different spectral sensitivities being used for the evaluation.

Below, the invention will be explained in more detail on the basis of exemplary embodiments, with use being made of the drawings.

Figure 5:
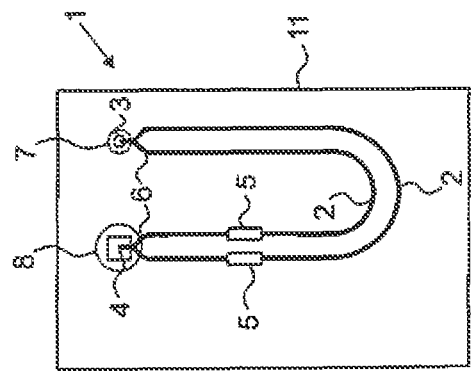
Figure 6:
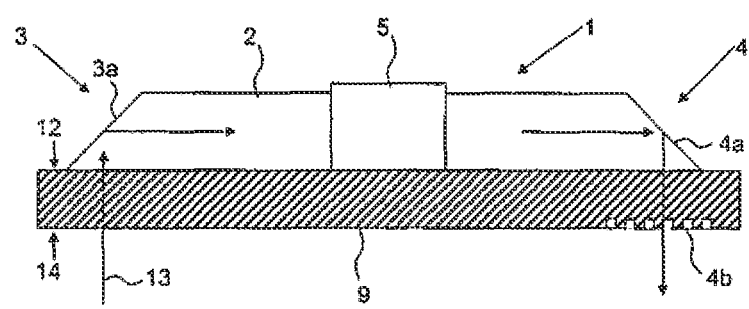
Figure 7:
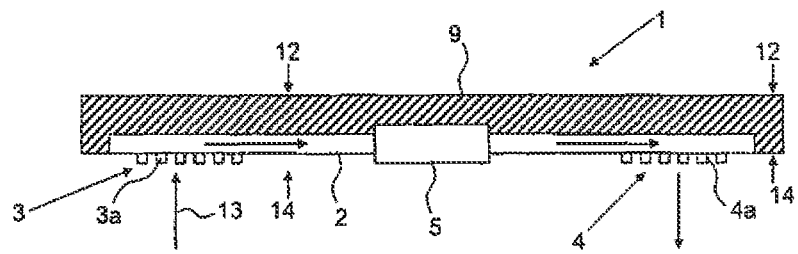
Figure 8:
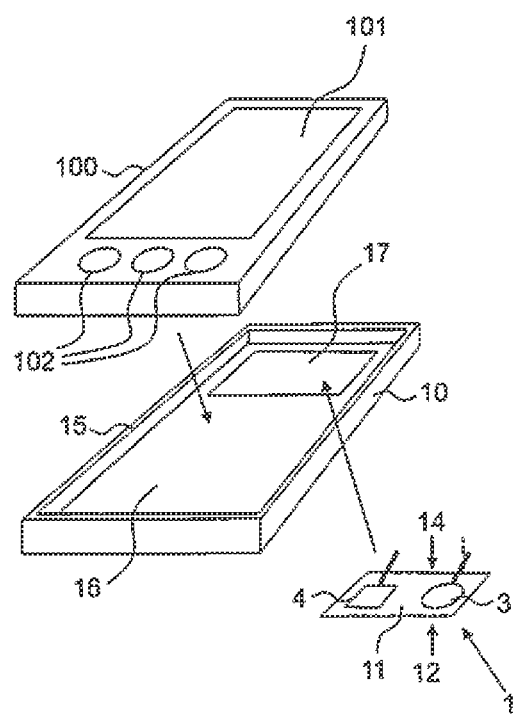
Figure 9:
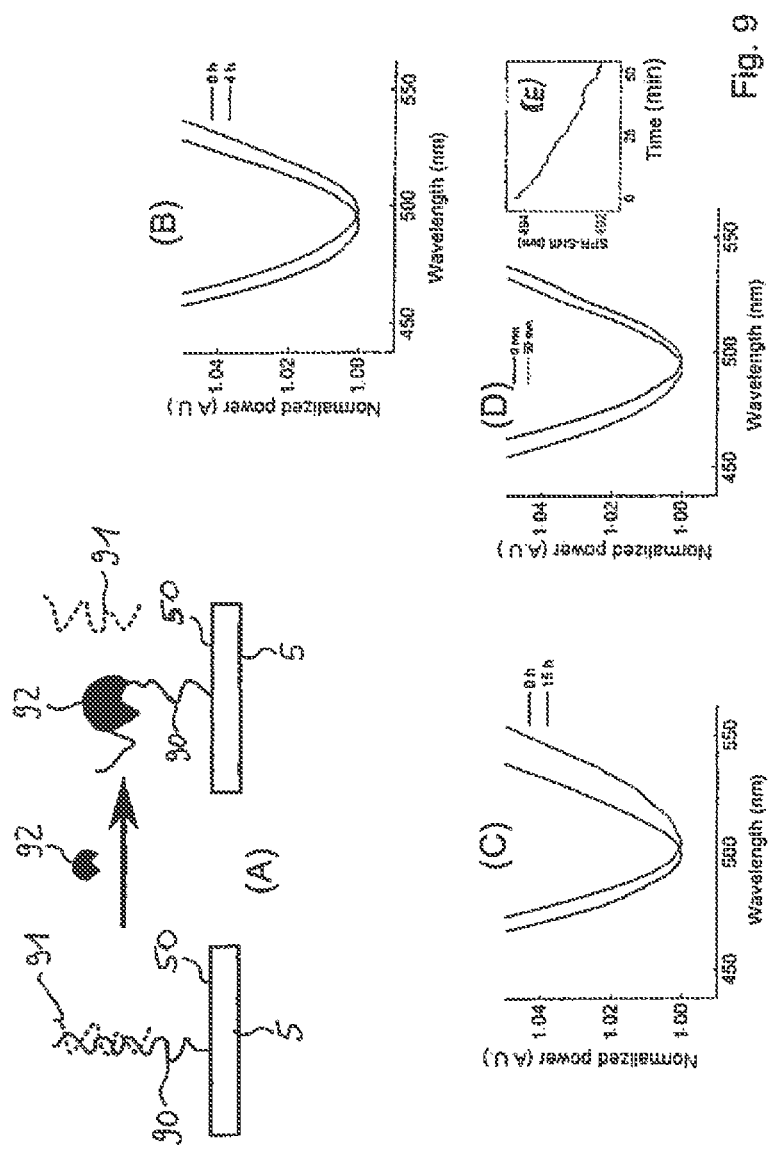
Figure 10:
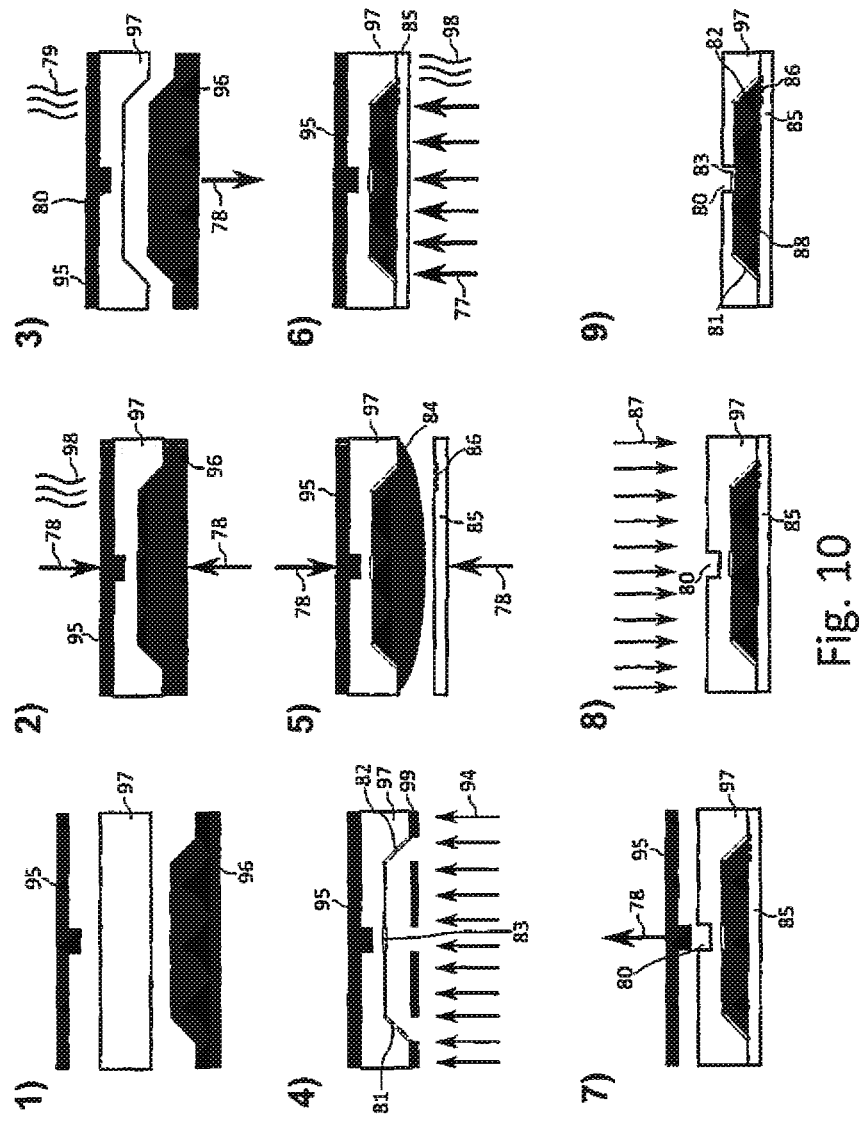
Figure 11:
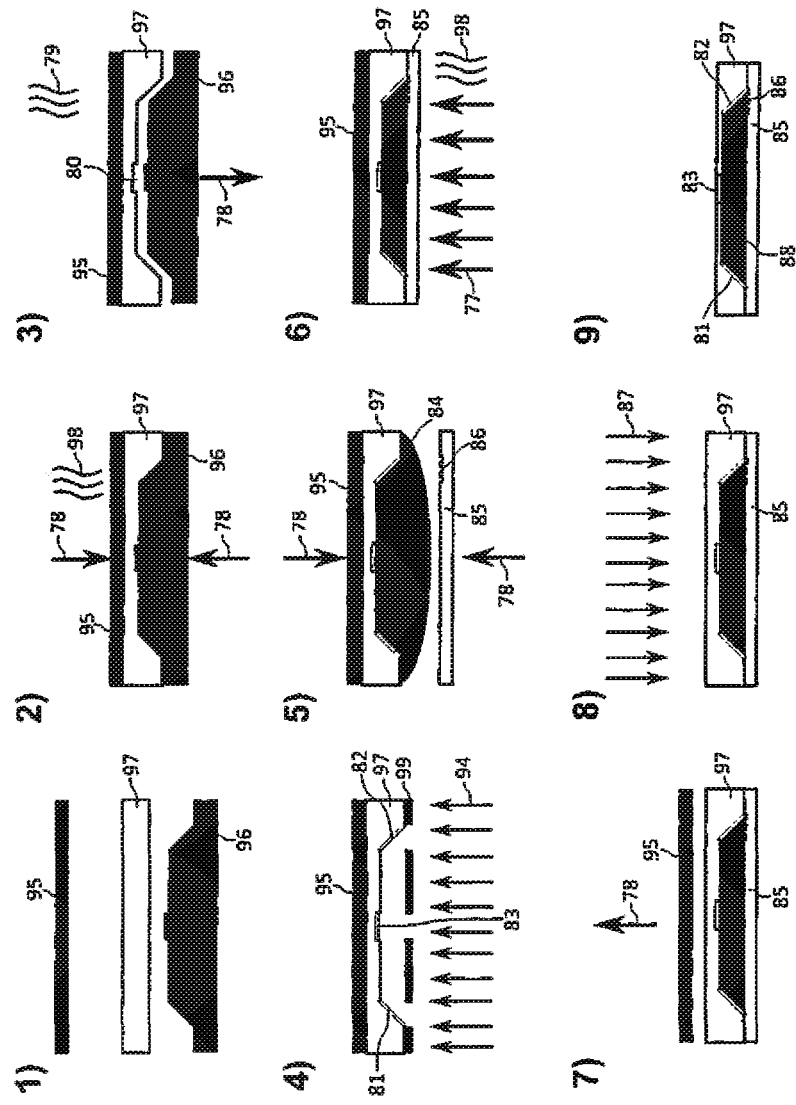
Figure 12:
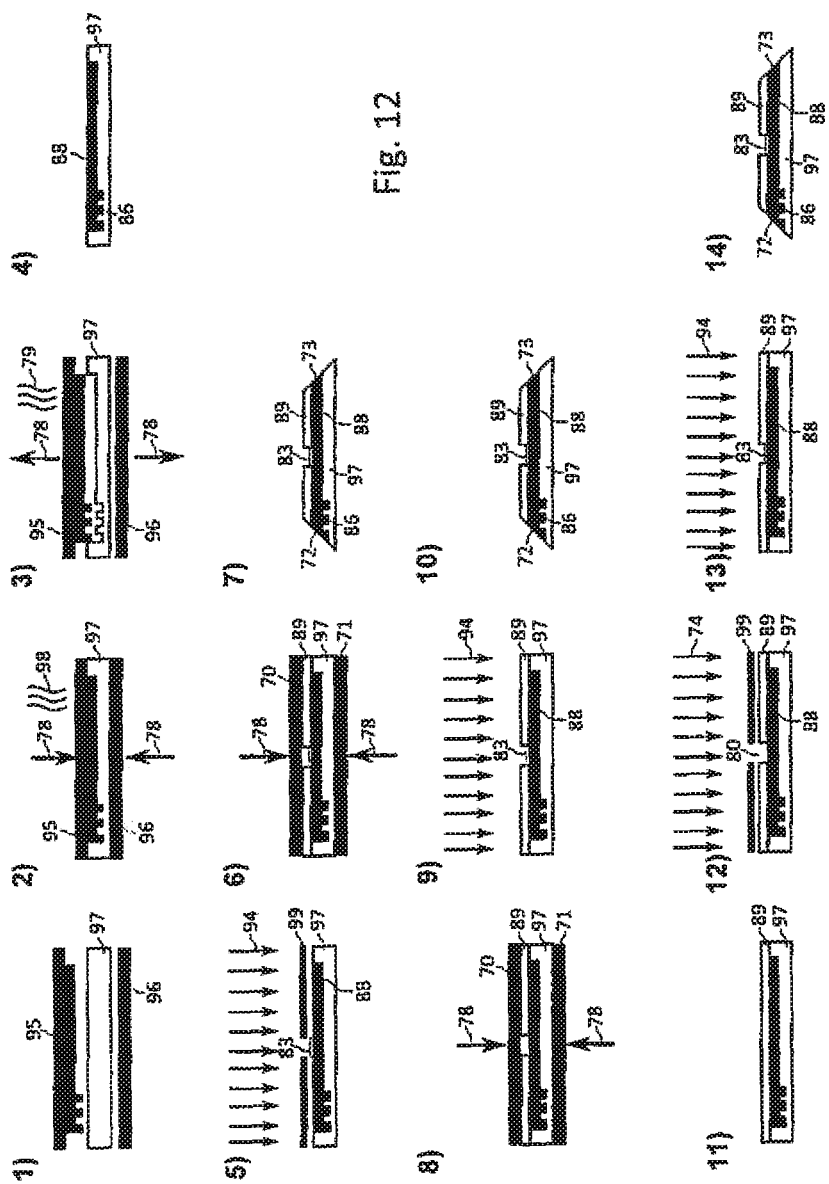
Figure 13:
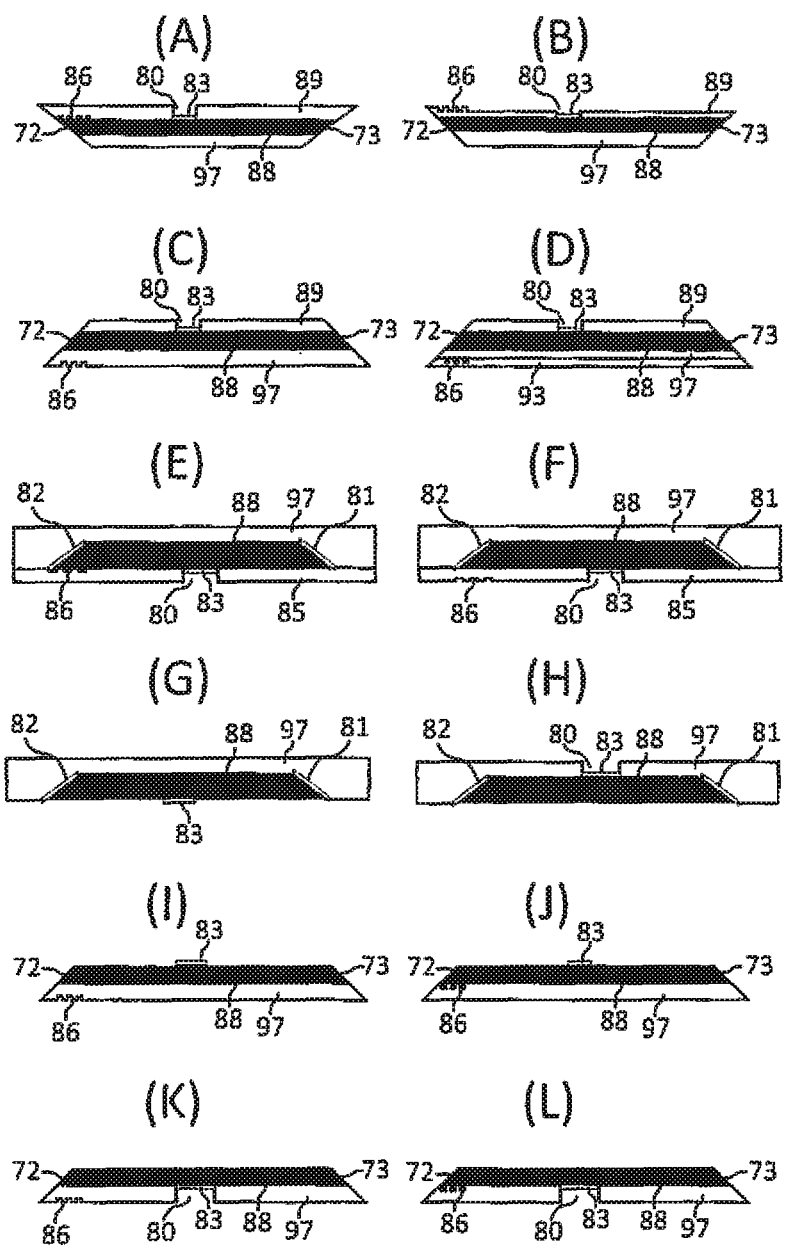
Figure 14:
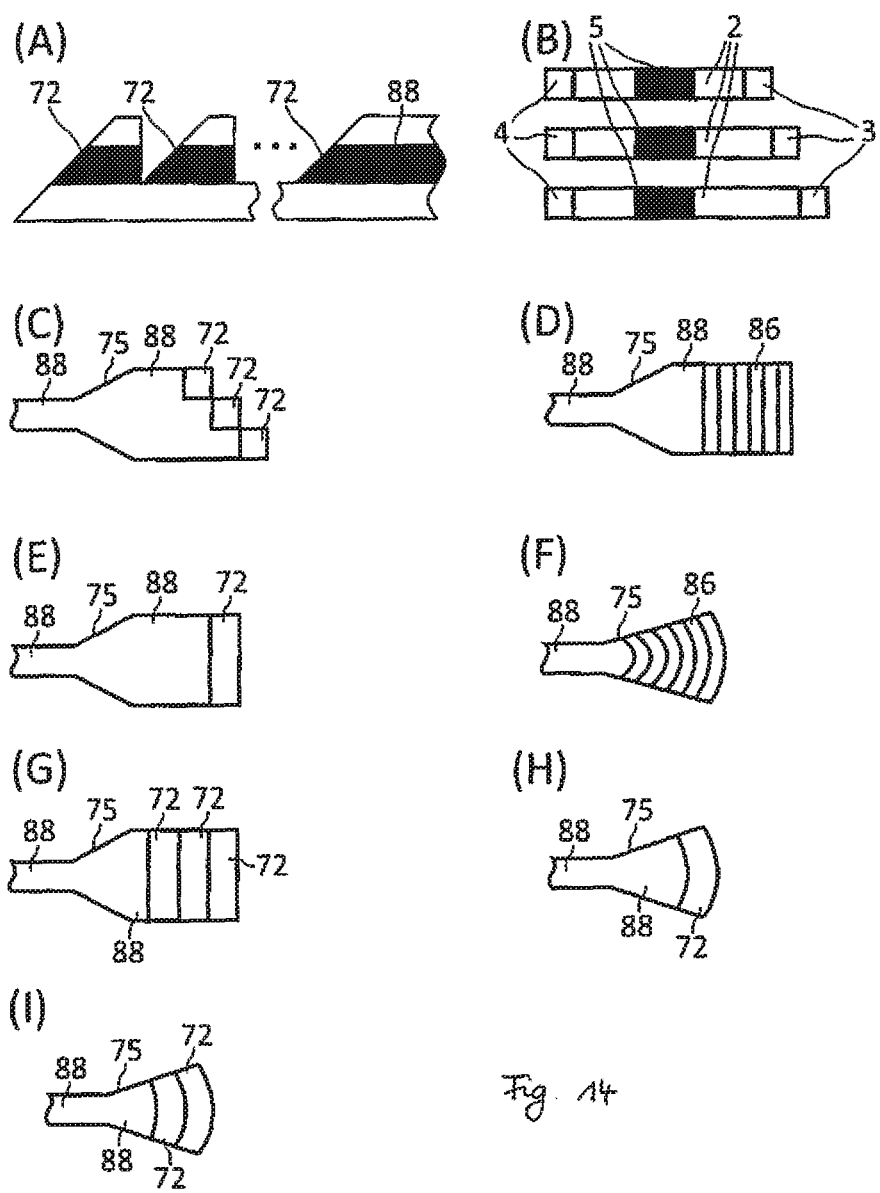
Figure 15:
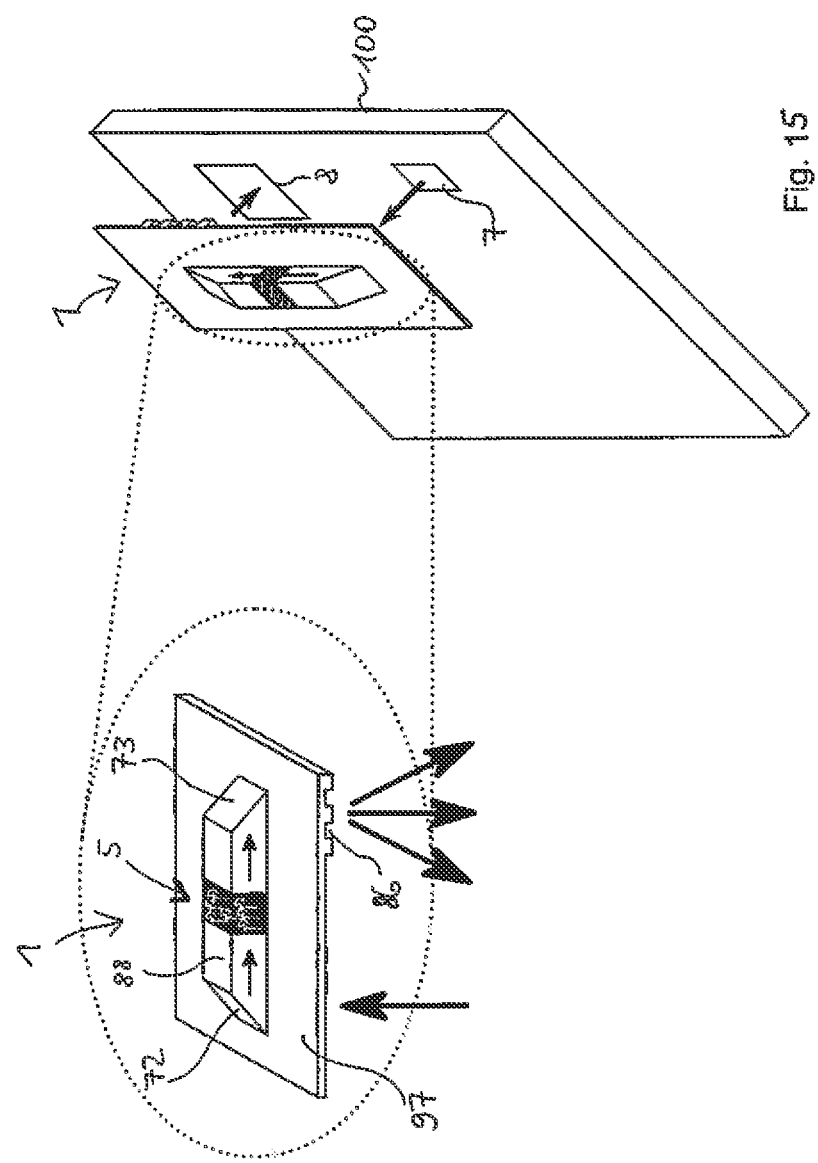
Figure 16:
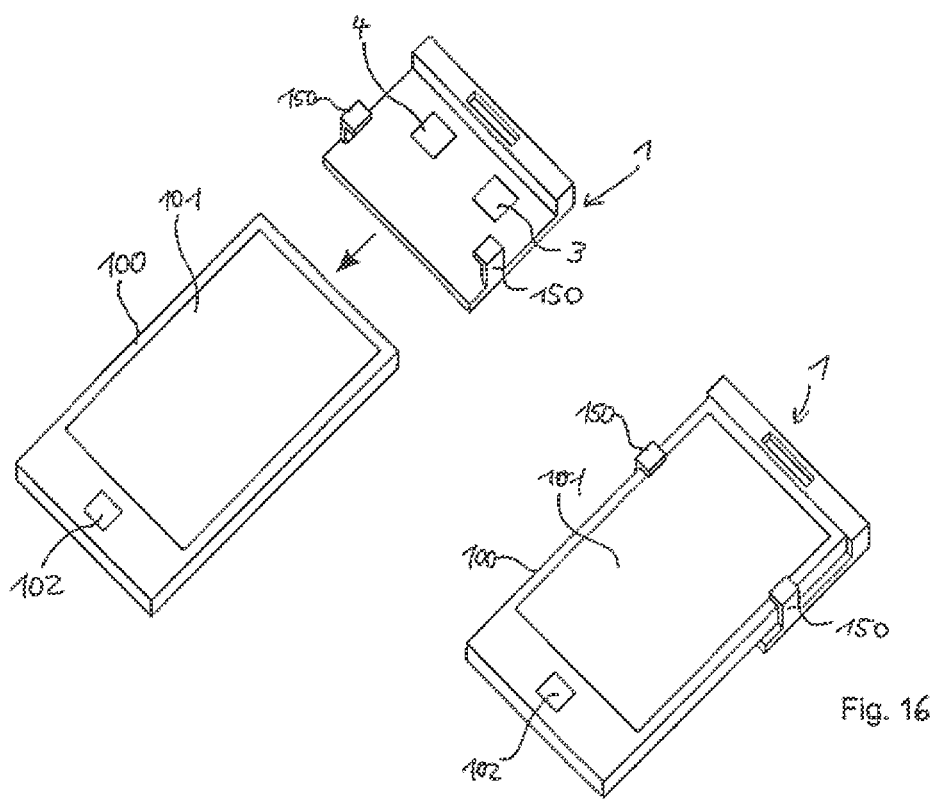
Figure 19:
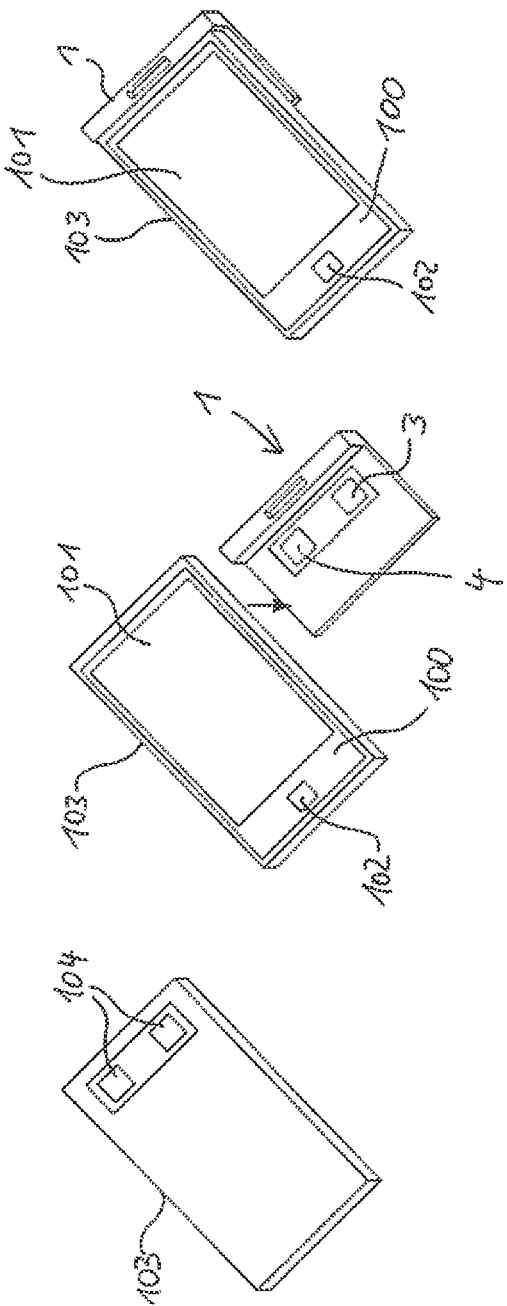
Figure 19:
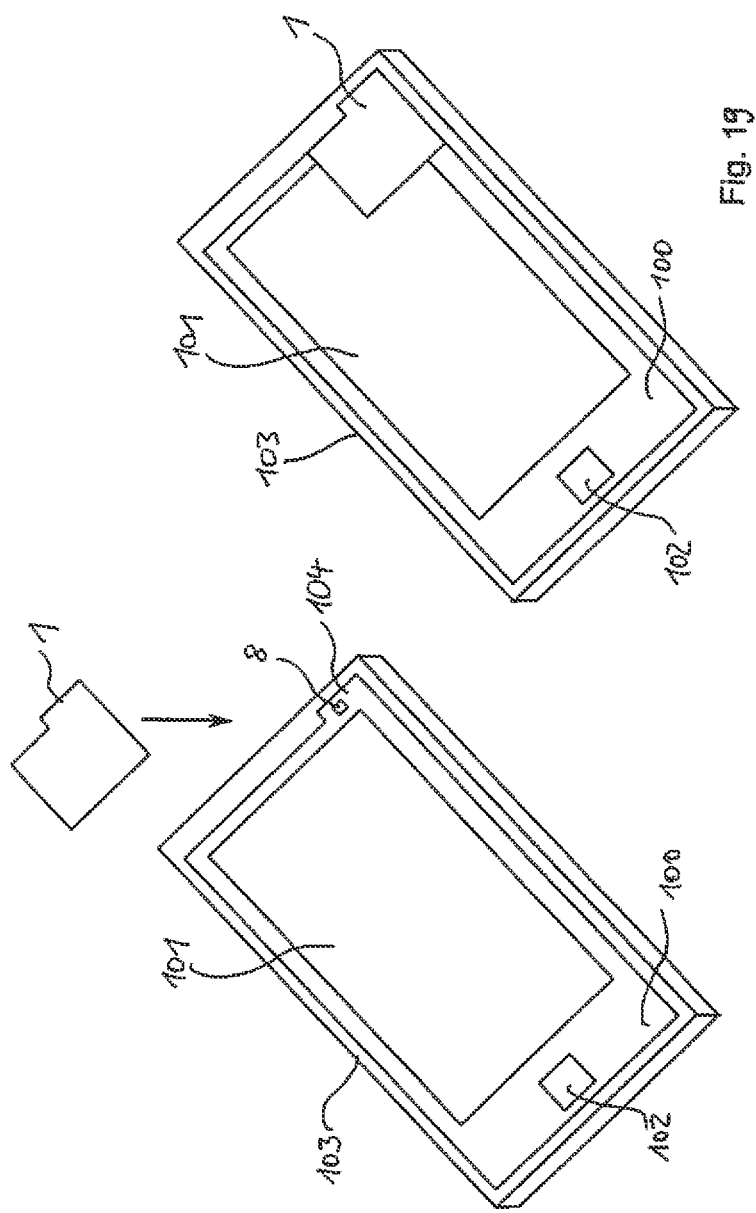
Figure 20:
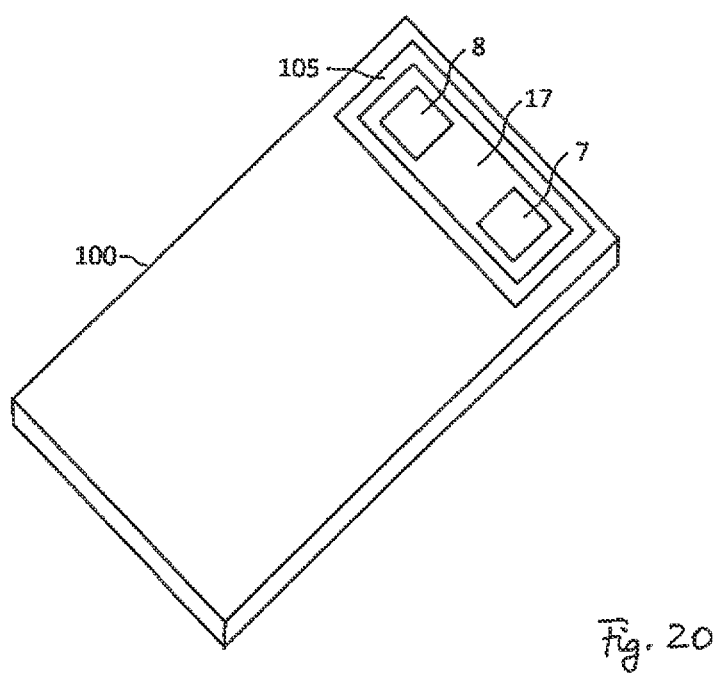

In the figures:

FIG. 1 shows a mobile computer appliance and an optical sensor system in a perspective illustration and FIGS. 2 to 5 show various embodiments of an optical sensor system in a plan view and FIGS. 6 and 7 show various embodiments of an optical sensor system in a side view and FIG. 8 shows a mobile computer appliance, a holding apparatus, and an optical sensor system in a perspective illustration and FIG. 9 shows a possible measurement principle of an aptamer-based sensor system and FIG. 10 shows a first production method for a sensor system and FIG. 11 shows a second production method for a sensor system, FIG. 12 shows a third production method for a sensor system and FIG. 13 shows possible design forms of a planar-optical sensor system and FIG. 14 shows possible further design forms and arrangements of the input and output coupling interface, FIGS. 15 to 17 show further embodiments of the sensor system and FIG. 18 shows a sensor system for interaction with a smartphone protective cover and FIG. 19 shows a smartphone protective cover for positioning the sensor system and FIG. 20 shows a holding apparatus for the sensor system.

Figure 21:
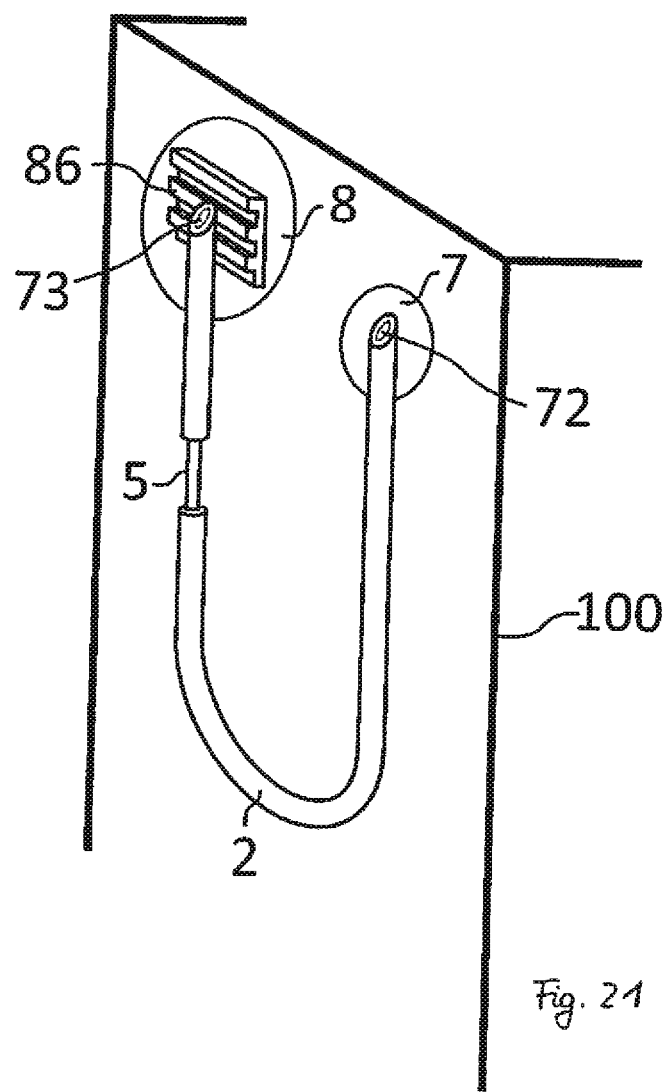

FIG. 21 shows a sensor system in the design form of an optical fiber and external optical components.

In FIGS. 2 to 7, the optical sensor system is presented in a partly cut manner in each case such that the elements that are integrated into the plane holding structure become visible. In the drawings, the same reference signs are used for elements that correspond to one another.

FIG. 1 shows a mobile computer appliance 100, for example a smartphone, which has e.g. a display 101 and operating elements 102 on its front side. Further, an optical sensor system 1 is presented, the latter being configured to interact with the mobile computer appliance 100. To this end, the optical sensor system has a holder 10, into which the computer appliance 100 can be inserted with exact fit, for example in a manner similar to a bumper for a smartphone. The holder 10 has in a receiving region, into which the computer appliance 100 is to be inserted, a plane holding structure 11 which delimits the holder 10 in the downward direction. Various optical components, which will still be explained below, are integrated into the plane holding structure, 11. In particular, an input coupling interface 3 for input coupling of light from the light source of the computer appliance 100 and an output coupling interface 4 for output coupling of light from the sensor system 1 to the camera of the computer appliance 100 are visible in FIG. 1.

It is further possible to identify that the plane holding structure 11 is embodied as a thin, flat structure with two main surfaces 12, 14 that face away from one another.

Figure 2:
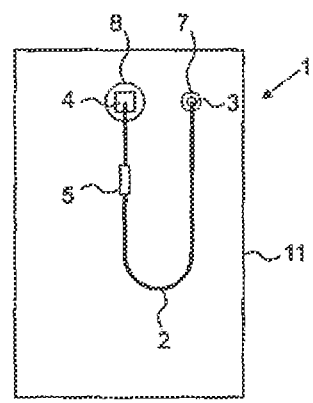

A first embodiment of the plane holding structure 11 is presented in a plan view in FIG. 2, with the plane holding structure 11 being opened up so far that the optical components arranged therein become visible, as illustrated in FIG.

2. It is possible to recognize that, proceeding from the input coupling interface 3, a light guiding path 2 which is formed by an optical waveguide, is guided downward and guided back again via a 180° arc to the output coupling interface 4. A sensor element 5, which is also referred to as sensor below, is arranged in the light guiding path 2. By means of the input coupling interface 3, light from the light source 7 of the computer appliance 100 is fed into the light guiding path 2 and guided through the sensor 5, and the emerging light is fed to the camera 8 of the computer appliance 100 by way of the output coupling interface 4.

Figure 3:
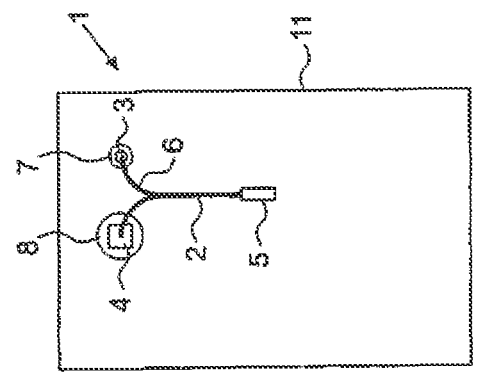

In a second embodiment, which is presented in FIG. 3, the light is not guided through the sensor 5 (transmission principle) like in the first embodiment; instead, it is reflected by the sensor 5 reflection principle). Therefore, in this embodiment, the light is guided, via a waveguide coupler 6, from the light source 7 via the input coupling interface 3 and via the light guiding path 2 to the sensor 5. The light reflected there is guided via the light guiding path 2 and the wave coupler 6 to the output coupling interface 4 and can accordingly be recorded by way of the camera 8.

Figure 4:
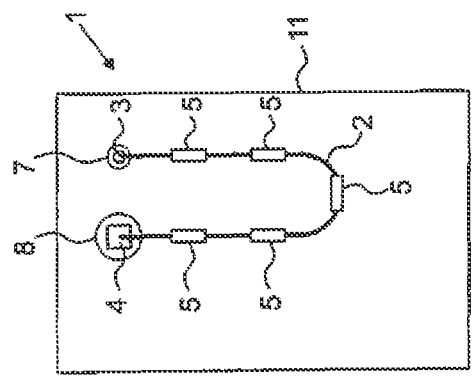

In a third embodiment, which is presented in FIG. 4, a plurality of optical sensors in this case a total of five, are arranged in succession in the same light guiding path 2. The signal capturing in the computer appliance 100 is carried out by way of optical multiplexing.

In a fourth embodiment, which is presented in FIG. 5, a plurality of light guiding paths, e.g. two light guiding paths 2, are arranged parallel to one another. At least one sensor 5 is arranged in each light guiding path. The light guiding paths 2 can be connected to the input coupling interface 3 and to the output coupling interface 4 by means of a respective waveguide coupler 6. Furthermore, the parallel light paths could each have a dedicated output coupling interface but a common input coupling interface.

As can be identified, the presented exemplary embodiments are not exhaustive. In principle, any number of sensors may be present in a light guiding path, just as, in principle, any number of parallel light guiding paths may be provided. Therefore, all exemplary embodiments can be combined with one another.

Further, the optical sensor system 1 may be realized in the form of a ridge waveguide (FIG. 6) or a buried waveguide (FIG. 7). FIG. 6 shows a light guiding path 2 in the form of an optical waveguide which is applied to a substrate 9 that serves as a holding structure. Once again, a sensor 5 is arranged in the light guiding path 2. In this case, the input coupling interface 3 comprises an input coupling member 3*a* that is embodied as a bevel of the optical waveguide, by means of which the incident light 13 is deflected. As an output coupling member, the output coupling interface 4 has a bevel 4*a* of the optical waveguide, by means of which the light is once again deflected. Further, the output coupling interface 4 comprises an optical grating 4*b* (diffraction grating) as a further output coupling member, the light being able to be divided into corresponding spectral components by way of said optical grating, and so the camera 8 of the computer appliance 100 can be used as a spectrometer.

In the embodiment as per FIG. 7, a light guiding path 2 is embedded into the substrate 9, which serves as a holding structure. Likewise, the sensor 5 is embedded in the light guiding path and the substrate 9. The input coupling interface 3 for entering light 13 comprises an, input coupling member 3 in the form of an optical grating 3*a*. The output coupling interface 4 comprises an output coupling member in the form of an optical grating 4*a*.

The presented courses of the light guiding paths 2 are only specified in an exemplary manner in each case. Depending on the realization of the sensor system, the courses may also have a different look. The sensor 5 or the plurality of sensors 5 can be arranged at any position along the light guiding path, and not only at the positions of a specified in an exemplary manner in the exemplary embodiments.

The output coupling interface 4 serves to couple the light guiding path 2 with the camera 8 of the computer appliance 100, wherein use can, be made of both the camera on the front side and the camera on the rear side. By way of example, the output coupling member can be composed of a prism, mirror, and/or optical grating. Furthermore, use can be made of a waveguide that is angled at 45°—with, or without an optical grating—wherein, inter alia, the light is deflected by total internal reflection. The light from the optical waveguide can be spectrally separated in space with the aid of the optical grating, and hence the spectral behavior of the optical sensor structure can be examined by means of the smartphone camera.

FIG. 8 shows a modified embodiment of the invention presented in FIG. 1. In contrast to FIG. 1, the holder 10 has on its support surface 16 a receiving region 17 for the sensor system 1. The sensor system 1 is embodied as a separate unit with a plane holding structure 11 (which is once again present), which can he inserted into the receiving region 17 together with the further components 3, 4 arranged thereon or therein.

By way of example, the optical components of the sensor system 1 can be produced by a printing method, by photolithography, by micro replication, by laser material processing, and/or by a combination of the aforementioned methods.

By way of example, polymeric, optical components can be produced by flexography, offset printing or inkjet printing. In view of micro-replication, the optical components are transferred into a substrate with the aid of a nanostructured mold. By way of example the structure transfer can be carried out by reaction injection molding, injection molding, injection compression molding, hot embossing, thermoforming or nanoimprint lithography. By way of example, hot embossing of micro-optical structures in polymer substrates is conventional method. In evacuated surroundings, a thermoplastic plastic is heated into its viscoelastic state and pressed into a nanostructured mold. The demolding is subsequently carried out after cooling. Virtually all thermoplastics and thermoplastic elastomers can be used for hot stamping.

By way of example, laser material processing contains the production of optical waveguides by laser-induced refractive index changes on the surface or in the volume of e.g. polymer substrates, or the production of micro-optical structures by laser ablation. By way of example, optical wave guide structures can be written into the polymer with the aid of a photomask and an excimer laser or by the mask-less laser direct writing method, for example by means of a femtosecond laser. Furthermore, the three-dimensional structuring of the optical sensor structure in plastics can be carried out by two photon polymerization (2PP).

Moreover, the optical components can be produced by laser-induced changes in, the refractive index on the surface or in the volume of glass substrates. Furthermore, the ion exchange method could be used to produce optical components in glass.

In view of the production of the optical components, it is possible, for example, for the input coupling interface 3 and the output coupling interface 4 and the optical waveguides to be initially produced or prepared by micro-replication in order subsequently for the production process of the optical beam path to be completed by the introduction of a polymer with a higher refractive index or an optical fiber or by waveguide printing or by laser material processing. Following the production of the optical beam path, the sensor structure is functionalized, optionally in accordance with the target parameter or the target parameters.

Within the scope of trials, a surface plasmon sensor system was developed on the basis of an optical glass fiber for environmental analysis for smartphones. A 400 μm plastic cladding silica (PCS) fiber with a length of 25 cm was used as an optical lass fiber. Both ends of the optical fiber were whetted at 45° in order to input couple light into the optical fiber, or output couple light from the optical fiber, perpendicularly by way of total internal reflection. The surface plasmon sensor was realized by a silver coating of the optical fiber core with a length of approximately 1 cm, with the optical fiber cladding at this position being removed in advance. The spectral components of the smartphone LED were imaged on the smartphone camera with spatial separation by means of a holographic PDMS diffraction grating between the end of the optical fiber and the smartphone camera. As a result of the spectral decomposition, it is possible to detect the resonance of the surface plasmon sensor and measure changes in the refractive index of the surroundings by the displacement of the resonance. Within the scope of the trials, it was already possible to obtain a sensitivity of $5.96 \times 10^{-4}$ units of refractive index/pixel. The sensitivity of the developed sensor system can be improved further by optimizing the output coupler and the diffraction grating.

Within the scope of trials, it was possible, by means of surface plasmons, to develop an optical sensor system for smartphones which has a high sensitivity in relation to changes in the refractive index. It is possible to measure a multiplicity of parameters by an appropriate functionalization of the sensor surface, integration of a measurement converter, which e.g. converts a change in gas concentration into a change in refractive index, and hence a large field of use is conceivable.

Possible future applications of such a disposable lab-on-a-chip could include e.g. a pregnancy test, a lactate test or the monitoring of the blood sugar content. A further field of application of the disposable lab-on-a-chip can be in travel medicine. Here, novel products can be developed with the aid of the link between a smartphone and a sensor system. By way of example, the disposable chip can be used for diagnosing and monitoring malarial infections. Furthermore, the disposable chip can serve to diagnose myocardial infarctions or instances of food poisoning on holiday trips. Since there is also an elevated concentration of enzymes and proteins (biomarkers) of the dying myocardium in the blood during a myocardial infarction in addition to strong chest pains, the patient can be warned by the detection of these biomarkers and the patient can be guided to the nearest emergency medical center with the aid of the GPS location data or the paramedic can be guided to the patient. Furthermore, new applications/products in veterinary medicine can be developed using a cost-effective sensor system that is based on a disposable chip.

It is possible to monitor environmental parameters or person-specific parameters using a sensor system which, for example, is integrated in a smartphone protective cover. Possible applications could include the continuous determination of ammonia and/or methane content in agriculture. Polyaniline or cryptophane A molecules that are introduced in PDMS can be used as measurement converters for ammonia or methane. Furthermore, the sensor system can be used to measure humidity, carbon dioxide, oxygen or nitrogen and hence monitor the indoor climate.

Furthermore, it is possible to develop a sensor system with an integrated dosimeter for measuring x-ray radiation. Energy doses of x-rays can be measured on the basis of a spectral damping and/or fluorescence measurement by means of e.g. PMMA fibers without/with a scintillator. By way of example, this renders it possible to ascertain the radiation exposure of radiologists and hence the smartphone dosimeter can be a cost-effective alternative to existing personal dosimeters. Moreover, smartphone users can measure their UV light exposure due to solar irradiation and can therefore protect themselves from sunburn.

The smartphone protective cover can also be integrated into pieces of clothing, with the piece of clothing being provided with fiber optical sensors. Hence, the smartphone protective cover serves to connect the smartphone to the fiber-optical sensor system in the piece of clothing. By way of example, possible applications in this case are the monitoring of the respiration of neonates using a top that has been provided with fiber-optical expansion sensors in order to detect possible apnea, or the measurement of blood pressure using a smartphone sphygmomanometer.

Further configurations of the invention and the advantages thereof:

Integration of optical waveguides and waveguide sensors into the smartphone protective cover for monitoring environmental parameters or person-specific parameters, wherein the smartphone LED and smartphone camera serve as light source and detector, respectively.

Optical waveguides and waveguide sensors in polymer substrates which can be used in combination with a mobile computer appliance, such as e.g. a smartphone/tablet, as a disposable lab-on-a-chip for laboratory diagnostics close to the patient. Since both the smartphone LED(s) or the display and the smartphone camera (on the front side or rear side) can be used as light source and detector, respectively, no active components are required for the operation of the disposable lab-on-a-chip. This yields a cost advantage in comparison with the prior art.

Multiplexing of a plurality of optical sensors and hence monitoring of a plurality of different parameters by means of only one sensor system.

Combination of integrated fiber-optical sensors in pieces of clothing and querying thereof by means of a smartphone.

In an advantageous embodiment of the sensor element 5, aptamers are immobilized on the sensor surface as specificity-imparting receptors. Aptamers are single-strand DNA or RNA oligonucleotides which can be generated in an iterative in vitro selection process called SELEX (Systematic Evolution of Ligands by EXponential Enrichment) against any target structure such as e.g. proteins, low-molecular connections or else whole cells. The aptamers can be coupled onto the sensor surface, inter alia e.g. chemically by way of linker molecules, applied thereon by means of self-assembled monolayers of thiol-modified aptamers, hybridized thereon at immobilized oligonucleotides that are complementary to portions of the aptamer or bound on the sensor surface purely by adsorption. The specific binding of the analyte to be detected to the aptamer can either lead directly to a change in the refractive index over the sensor surface or else it is possible to use indirect methods for generating a change in refractive index. An exemplary option for indirect generation of a change in refractive index, which, in particular, is also suitable for the analysis of small molecules, lies in the use of oligonucleotides that are complementary to the target binding site of the aptamer. In this exemplary embodiment, the aptamer 90 is immobilized on, the sensor surface 50 of the sensor element 5 and subsequently hybridized with the oligonucleotide 91 that is complementary to the target binding side of the aptamer 90; see FIG. 9(A), left-hand side. When the sample is measured, the target 92 binds to the aptamer 90 and displaces the oligonucleotide 91 from the aptamer 90; see FIG. 9(A), right-hand side. Here, the displacement of the oligonucleotide leads to a measurable change in the refractive index. In addition to this sequential sequence of 1. hybridization, of the complementary oligonucleotide and 2. displacement of the oligonucleotide by the target, it is also possible to bring the immobilized aptamer into contact with a mixture of the oligonucleotide and the target in a directly competitive approach. In this case, the amount of the hybridized oligonucleotide, and hence the change in the refractive index, is dependent on the concentration of the target.

The option for applying aptamers as specificity-imparting receptors for functionalizing the sensor surface was demonstrated in an exemplary manner using the example of the aptamer-based detection of ethanolamine. To this end, a silver-coated fiber-optical sensor was initially modified with mercaptoundecanoic acid (MUA) as a linker molecule. To this end, a 200 mM MUA solution in 100% ethanol was used. The MUA modification was subsequently activated with a mixture of 100 mM 1-Ethyl-3-(3-dimethylaminopropyl)carbodiimide (EDC) and 100 mM N-hydroxysucoinimide (NHS) in 50 mM 2-(N-morpholino)ethanesulfonic acid (MES). The 5'-terminal amino-modified aptamer EA#14.3 (100 μM in 50 mM MES which is directed to ethanolamine, was bound to the the activated surface.

The immobilized aptamer against ethanolamine was subsequently incubated with an oligonucleotide that is complementary to the target binding site of the aptamer. A red shift of the resonance of the sensor by 7 nm was observed during the hybridization between the aptamer and complementary oligonucleotide; see FIG. 9(C). This elucidates that the sensor is also able to detect relatively small molecules since the employed oligonucleotide had a molecular weight of only 4668 Da. Subsequently, the sensor was incubated with ethanolamine (10 μM in 20 mM tris(hydroxymethyl)aminomethane (tris), 100 mM NaCl, 0.02% Tween (pH 7.6)). The ethanolamine-induced displacement of the complementary oligonucleotide from the aptamer resulted in a blue shift of the resonance of the sensor by 2.2 nm; see FIG. 9 (D). Hence, the detection of a very small molecule (molecular weight of ethanolamine: 61 Da) could be realized indirectly by the displacement of the complementary oligonucleotide.

Overall, it was possible to show that the SPR sensor can be functionalized with aptamers, the latter maintain their binding properties in the process and the SPR-based aptasensor thus generated is able to detect also relatively small molecules which only lead to small changes on the sensor surface.

FIG. 9(A) shows a schematic illustration of the measurement principle. The aptamer 90 is immobilized on the sensor 5 and a complementary oligonucleotide 91 is hybridized onto the aptamer 90. This oligonucleotide is displaced by an ethanolamine, as a result of which the optical density over the sensor 5 is reduced. This can be read as a shift in the resonance. Shifts in the resonance, during the functionalization of the sensor and the detection of ethanolamine are identifiable in FIG. 9(B). A displacement by 6.7 nm was observed during the immobilization of the aptamer (100 μM). The hybridization of the oligonucleotide (100 μM) likewise led to a red shift of the resonance by 7 nm, as may be identified in FIG. 9(C). The displacement of the oligonucleotide by ethanolamine (10 μM) led to a blue shift of the resonance by 2.2 nm, as may be identified in FIG. 9(D). The time profile of this shift shows that a clear signal is already obtained within 30 minutes, as is identifiable in FIG. 9 (E).

The embodiment of the sensor, presented here, for the aptamer-based detection of ethanolamine constitutes an example for detecting a small molecule. By using other aptamers, which specifically bind to further small molecules such as e.g. antibiotics, toxins or others, and corresponding oligonucleotides that are complementary to the binding site of the employed aptamers, it is possible to realize sensors with any specificity.

In addition to the detection of small molecules, presented above, the aptamer-based sensors can also be designed for the detection of relatively large analytes such as e.g. proteins, viruses, bacteria or others. In this case, a complementary oligonucleotide can be dispensed with if the aptamer-imparted binding of the analyte to the sensor surface leads to a sufficiently large change in the optical properties of the medium over the sensor surface. Alternatively, it is also possible to use measures for signal amplification for relatively large analytes such as e.g. proteins, viruses, bacteria or others. Thus, it is possible to use e.g. aptamer-modified nanoparticles which bind to the analytes that are bound to the sensor surface via aptamers. As a result, the nanoparticles are positioned in the vicinity of the sensor surface and serve for signal generation and/or signal amplification.

Exemplary production steps for a possible design of the sensor system are presented in FIGS. 10 and 11. At the start of the production, the basic structure of the sensor system is thermally formed in a polymer basic substrate 97 by means of two dies 95, 96 (hot stamping method with a heat supply 98). The waveguide structure and coupler basic structure are produced with the aid of the lower die 96. The upper die 95 could produce a recess 80 in the polymer basic substrate 97, which subsequently serves as analysis window of the sensor, with the analysis window 83 in this case defining the region of the interaction between the optical sensor and the surroundings (functionalization), Poly (methyl methacrylate) (PMM) and/or cyclic olefin copolymer (COC) with refractive indices of 1.49 and 1.53, respectively, could be used as polymer basic substrate 97. Subsequently, the lower die 96 is removed. By way of example, this may be carried out by cooling 79 (steps 1-3).

Due to the process, a residual layer of substrate material might remain between waveguide core and analysis window, although this could he removed in a subsequent step. Moreover, the remaining residual layer could serve in a targeted manner as a sacrificial layer for applying the metallization layer that is required for the plasmon sensor. In the subsequent production step 4, the basic structure of the plane optical waveguide in the polymer basic substrate 97, which is now present, could he coated with metal, for example by, means of a sputtering or evaporation method 94. The metal coating could be used to realize the optical coupler and produce the SPR sensor, in order only to coat the mirror regions 81, 82 and the analysis window 83 of the optical sensor, all other regions could be masked by way of a mask 99.

After the coating with metal, a liquid monomer 84, which has a higher refractive index than the polymer basic substrate and which, inter alia, but not necessarily, can be cured or polymerized by means of UV radiation and which forms the optical waveguide core after the polymerization, is placed into the basic structure of the waveguide of the polymer basic substrate 97 (step 5). In step 6, a base substrate 85, which, has a lower refractive index than the optical waveguide core, may be pressed onto the basic structure of the waveguide of the polymer basic substrate 97 with the liquid monomer 84 using a force F 78 of several kN and it may be polymerized, for example by means of UV irradiation 77. Here, the base substrate 85 could already contain the grating structure 86 for the spectrometer that was produced previously, for example by means of a hot stamping method or material processing (e.g. ablation by means an excimer laser). The grating could also be introduced later into the lower side of the base, substrate at the end of work step 6 or at the end of the production method, for example by means of a hot stamping method or material processing. Alternatively, the waveguide core and the base substrate could be applied in steps 5 and 6, for example by means of spin coating, and/or, if necessary, the grating could be, introduced later into the lower side of the base substrate. In production step 7, the upper stamp 95 is removed and, if necessary, the remaining residual layer on the analysis window 83 of the optical sensor can likewise be removed in subsequent work step 8 and the analysis window can be exposed. By way of example, the analysis window of the optical sensor can be exposed with the aid of an oxygen plasma 87. Alternatively, use could also be made of e.g. an excimer laser (laser ablation) or solvent, such as e.g. chloroform or toluene. Furthermore, exposing could also be carried out in a masked manner. Moreover, the optical sensor can be sensitive to polarization. A non-polarized light source of the computer appliance can be linearly polarized by the application of a polarizer, for example in the form of an iodine-doped polyvinyl alcohol (PVA) film, for example between the light source and input coupling interface.

The base substrate is appropriately prepared prior to work step 5 and it may contain a grating on the upper side and/or lower side. Furthermore, a metal film could alternatively he applied to the upper side of the base substrate. In this case, the metal coating at the site of the analysis window of the optical sensor in work step 4 would no longer be necessary. However, the analysis window of the optical sensor would have to be exposed on the lower side of the plane optical sensor system in work step 8. The optical grating could also be produced into the lower side of the plane optical sensor system after the production with the aid of appropriate material processing methods. Furthermore, it would also be possible for a polymer film 93 with an optical grating 86 to be produced separately, which polymer film can be adhesively bonded onto the lower side following the production method of the plane optical sensor system (in this case without optical grating) (as shown in an exemplary manner in FIG. 13(D)).

In the method in accordance with FIG. 10, the recess 80 on the upper side of the polymer basic substrate 97 is produced by means of the upper die 95; in the method in accordance with FIG. 11, the recess 80 on the lower side of the polymer basic substrate 97 is produced by means of the lower die 96.

A further possible production method is presented in FIG. 12. Initially, the basic structure (with/without grating) of the optical light path is formed into a polymer basic substrate 97 and the waveguide core material 88 is introduced, for example by means of doctoring or spin coating (steps 1-4).

Steps 5-7: Then, for example, it is possible, where necessary, to coat the upper side of the waveguide 88 with a metal or a metal alloy 94 (the coating can be carried out in a masked manner by means of a mask 99) and a further polymer substrate 89 can be placed onto the upper side of the waveguide 88 and pressed on by means of two stamps 70, 71. By way of example, the polymer substrate 89 may be applied by means of a hot stamping method or bonding method and may already contain a recess 80 for the analysis window of the optical sensor. Alternatively, the polymer substrate 89 can also applied to the upper side by means of spin coating and the recess 80 for realizing the analysis window 83 can be produced, for example, with the aid of a mask and a plasma. The optical 45° coupling members 72, 73 can be produced with the aid of a whetting technique, a cutting method, a subsequent hot stamping method or a material processing method.

Steps 8-10: As an alternative to steps 5-7, the polymer substrate 89 could initially also be applied to the upper side of the waveguide 88 by hot stamping, adhesive bonding and/or spin coating. The polymer substrate 89 on the upper side could already contain a recess 80 for the analysis window of the optical sensor. Subsequently, the optical waveguide could be coated at the site of the recess with a metal or metal alloy 94 and the optical coupling members could be produced. The optical 45° coupling members 72, 73 could be produced with the aid of a whetting technique, a cutting method, a subsequent hot stamping method or a material processing method. Alternatively, the optical 45° coupling members could also be produced first and the coating with a metal or a metal alloy could then be carried out such that the optical 45° coupling members are likewise coated.

Steps 11-14: As an alternative to steps 5-7, the polymer substrate 89 could initially also be applied to the upper side by hot stamping, adhesive bonding and/or spin coating. The recess 80 for the analysis window of the optical sensor could be produced later, for example with the aid of a mask 99 and a plasma 74. Subsequently, the optical waveguide at the site of the recess could be coated with a metal or a metal alloy 94 and the optical coupling members could be produced. The optical 45° coupling members 72, 73 could be produced with the aid of a whetting technique, a cutting method, a subsequent hot stamping method or a material processing method. Alternatively, the optical 45° coupling members could also be produced first and the coating with a metal or a metal alloy could then be carried out such that the optical 45° coupling members are likewise coated.

Following the production of the plane optical sensor system, the corresponding functionalization of the sensor element 5 is carried out in the region of the analysis window and a fluidic/microfluidic system is applied in the case of a lab-on-a-chip. Here, the fluidic/microfluidic system can be used for functionalizing the optical sensor in one possible design. Moreover, the fluidic/microfluidic system could already be integrated into the polymer basic substrate 97 and/or base substrate 85 or it could also be integrated into the polymer basic substrate 97 and/or base substrate 85 during the production of the optical sensor system.

Further possible designs of the plane optical sensor system are presented in FIG. 13. These can be produced by an appropriate combination of different work steps of the production methods shown in FIGS. 10 to 12.

The production methods presented in FIGS. 10-12 can also be used to produce an optical sensor system with a plurality of optical sensors that are nested in series and/or in parallel.

The presented sensor surfaces can be modified prior to functionalization, e.g. by chemical treatment for the purposes of influencing the properties of the surface (hydrophobicity, non-specific binding, etc.).

The production methods and designs presented in FIGS. 10-13 show exemplary optical sensors that are based on surface plasmons. By leaving out the metal coating at the site of the optical sensor, it would also be possible to realize other optical sensors, such as e.g. an optical evanescence field sensor or a Mach-Zehnder waveguide sensor.

The 45° coupling elements presented in FIGS. 10-13 could also have a parabolic embodiment in order to optimize the light coupling between the optical sensor system and the external light source and/or the camera.

The designs presented in FIGS. 10-13 may, moreover, also contain taper structures and/or waveguide couplers. Waveguide couplers are necessary, inter alia, for realizing a Mach-Zehnder waveguide sensor and, furthermore can be used for coupling a plurality of parallel waveguides sensors at one input coupling interface. Moreover, the designs presented in FIGS. 10-13 may also be embodied without an optical grating 86.

Depending on the application case, the optical waveguides of the designs shown in FIGS. 10-13 may also have an arcuate embodiment and the recesses for the sensor element may have any three-dimensional structure.

FIG. 14 shows further possible designs and arrangements of the input coupling interface and output coupling interface of the sensor system. By way of example, the input coupling interface 3 in FIG. 14(A) is composed of a plurality of 45 degree input coupling members that are arranged in series along the tapered/non-tapered optical waveguide such that a uniform optical sensor system can be used for different smartphones or mobile computer appliances. In FIG. 14(B), a sensor system consists of a plurality of parallel sensor systems, with the lengths of the optical sensor systems varying such that the respective input coupling interfaces are situated at different locations and hence at least one optical sensor system is ideally aligned in relation to the light source 7 and the camera 8 at all times, even if the position of these components varies depending on smartphone or mobile computer appliance. In FIG. 14(C), the input coupling interface 3 is composed of a plurality of parallel 45 degree input coupling members and a tapered optical waveguide, wherein the 45 degree input coupling members may also be arranged with a slight offset.

Here, the reference signs employed therein in each case denote the following:
72 Optical 45° coupling member
73 Optical 45° coupling member
75 Taper structure
80 Recess for the sensor element
83 Analysis window of the optical Sensor
86 Optical grating
88 Optical waveguide
89 Polymer substrate
97 Basic structure of the sensor system FIG. 15 shows a sensor system 1 that was produced in accordance with one of the production methods explained above and the arrangement of said sensor system on a mobile computer appliance 100.

FIG. 16 shows an embodiment of the sensor system with a holding apparatus which has a particularly compact embodiment and only covers part of the computer appliance 100. By way of example, holding clips 150 are provided for fastening purposes, said holding clips fixing the holding apparatus with the sensor system 1 on the computer appliance 100 by engaging over the front side of said computer appliance.

FIG. 17 shows an embodiment of the sensor system with a holding apparatus which covers a projecting measurement tip 106 and only covers part of the computer appliance 100. By way of example, holding clips 150 are provided for fastening purposes, said holding clips fixing the holding apparatus with the sensor system 1 on the computer appliance 100 by engaging over the front side of said computer appliance.

On the left-hand side, FIG. 18 shows a protective cover 103 for a computer appliance 100, for example for a smartphone. The protective cover 103 is presented from the rear side in the left-hand image of FIG. 16, and so it is possible to identify that an appropriate notch 104 is provided on the rear side for positioning and/or fixing the holding apparatus with the sensor system 1 thereon. In FIG. 16, center, the protective sleeve 103 is presented from the front side with a computer appliance 100 inserted therein. On the rear side, the sensor system 1 can be attached to the protective sleeve 103 by means of a holding apparatus, as presented on the right-hand side in FIG. 16. The sensor system 1 with the holding apparatus comprises a design that corresponds to the notch 104 and is assigned as a counter piece such that the sensor system 1 with the holding apparatus can be used in conjunction with a computer appliance 100 arranged in the protective sleeve 103.

In FIGS. 16, 17 and 18, the sensor system can be connected to the holding apparatus in a permanent or interchangeable manner. Hence, in accordance with a further embodiment, the sensor system 1 may be embodied in the form of a disposable lab-on-a-chip, which can be affixed in the holding apparatus in a replaceable manner. Moreover, lenses and/or an optical grating or an FT spectrometer could be securely installed on the holding apparatus, and so the sensor system 1 need not contain these components and hence is able to be realized in a particularly cost-effective manner.

FIG. 19 once again shows a protective sleeve 103 from the front side, with a computer appliance 100 inserted into the protective sleeve. The protective sleeve 103 has a notch 104 which is arranged in the front side. This facilitates positioning and/or affixation of the sensor system 1 on the front side of the computer appliance 100. In an exemplary manner, FIG. 17 shows a notch 104 in the region of the camera 8 of the computer appliance 100; however, the notch can also e.g. additionally expose the light source 7 of the computer appliance 100. Alternatively, or additionally, the display 101 of the computer appliance 100 can be used as a light source.

FIG. 20 shows a holding apparatus, for example with or without magnetic fastening, in the form of a frame 105 which, for example, can be fastened to the rear side of a computer appliance 100, for example by adhesive bonding. This holding apparatus 105 serves for positioning and/or affixing the sensor system. In this case, no separate protective sleeve is required for positioning and/or affixing the sensor system on the computer appliance.

FIG. 21 shows the sensor system 1 in the form of an optical fiber 2 with a 45 degree input coupling interface 72 and a 45 degree output coupling interface 73 and an external optical grating 86 (diffraction grating). The external optical grating 86 moreover could also contain lenses. Furthermore, the 45 degree input coupling interface 72, the 45 degree output coupling interface 73, the optical grating 86 and lenses could be integrated in a separate polymer chip which could serve as a coupling element between the optical fiber with sensor element(s) and the mobile computer appliance.

The invention claimed is:

1. An optical sensor system configured to interact with a mobile computer appliance that comprises at least one light source and at least one camera, comprising:
   at least one input coupling interface for input coupling of light from the light source of the computer appliance;
   at least one output coupling interface for output coupling of light from the optical sensor system to the camera of the computer appliance;
   at least one optical light guiding path which couples the at least one output coupling interface to the at least one input coupling interface;
   at least one optical sensor element arranged in the at least one optical light guiding path configured to detect a physical input signal and produce an optical output signal based on the physical input signal; and
   a flatly constructed, planar holding structure into which the mobile computer appliance is insertable,
   wherein the holding structure is configured to hold the mobile computer appliance such that the at least one light source is located at a defined position relative to the at least one input coupling interface and such that the at least one camera is located at a defined position relative to the at least one output coupling interface, and
   wherein the at least one input coupling interface, the at least one output coupling interface, one or more elements of the at least one optical light guiding path, and the at least one sensor element are structurally integrated with the holding structure and are configured in a fixedly predetermined optical arrangement.

2. The sensor system as claimed in claim 1, wherein the holding structure is embodied as a thin, flat structure with two main surfaces facing away from one another, said two main surfaces being outer surfaces of the holding structure with a greatest area, wherein the two main surfaces extend substantially parallel to one another.

3. The sensor system as claimed in claim 1, wherein the holding structure has a thickness that is substantially less than a width and length of the holding structure.

4. The sensor system as claimed in claim 1, wherein the at least one optical light guiding path that is configured for for substantially parallel light guidance along two main surfaces of the holding structure.

5. The sensor system as claimed in claim 1, wherein the at least one light guiding path comprises at least one optical waveguide fitted along an arc in the holding structure.

6. The sensor system as claimed in claim 1, wherein the at least one light guiding path comprises one or more of
   an input coupling member for input coupling of light into the at least one light guiding path at the at least one input coupling interface; and
   an output coupling member for output coupling of light from the at least one light guiding path at the at least one output coupling interface,
   wherein one or more of the input coupling member and the output coupling member is configured to at least partly deflect light in a direction perpendicular to a main surface of the holding structure.

7. The sensor system as claimed in claim 1, wherein the plane structure comprises at least one mechanical fixation device which assists in arrangement and/or adjustment of the computer appliance relative to the holding structure.

8. The sensor system as claimed in claim 1 wherein the sensor system is configured so as to be integrated into, or embodied as, a protective cover of the computer appliance, a piece of clothing, or packaging.

9. The sensor system as claimed in claim 1 wherein the at least one light guiding path has at least one part that is integral with at least one part of the holding structure.

10. The sensor system as claimed in claim 1 wherein the at least one sensor element comprises a plurality of sensors that are arranged in succession or in parallel in a same light guiding path.

11. The sensor system as claimed in claim 1 wherein the at least one sensor element comprises at least one sensor region, on which, as receptors for sensing an analyte to be detected, aptamers, antibodies or other specificity-imparting structures, which are synthetically generated in relation to the analyte to be detected, are arranged.

12. The sensor system as claimed in claim 11, wherein the aptamers, antibodies or other specificity-imparting structures are aptamers, antibodies or other specificity-imparting structures that are wholly or partly marked for signal amplification.

13. The sensor system as claimed in claim 1 further comprising a Fourier transform spectrometer for detecting light emitted from the at least one sensor element.

14. The sensor system as claimed in claim 1 further comprising a fluidic or microfluidic system for guiding dissolved analytes toward the at least one sensor element.

15. The sensor system as claimed in claim 1 further comprising a cavity in a region of the at least one sensor element, said cavity being embodied as an absorption chamber with or without resonator properties.

16. The sensor system as claimed in claim 1 wherein the holding structure is adjustable in at least one spatial dimension in respect of an effective size of a receiving region for the mobile computer appliance.

17. The sensor system as claimed in claim 1 wherein one or more parts of the sensor system which cover the at least one light source of the mobile computer appliance, or one or more parts of the sensor system which cover the camera is adjustable in relation to the holding structure.

18. The sensor system as claimed in claim 1 wherein one or more parts of the sensor system which cover the at least one light source of the mobile computer appliance, or one or more parts of the sensor system which cover the camera is matched to the mobile computer appliance in such a way that the at least one light source and/or the camera is/are only partly covered.

19. A computer program encoded on a nontransient memory and which is executable on a computer appliance that interacts with the sensor system as claimed claim 1 that is configured to actuate a light source of a mobile computer appliance connected to the sensor system in a manner modulated with a predetermined modulation scheme and, further, in a manner to demodulate light received by a camera of the mobile computer appliance connected to the sensor system with a demodulation scheme that is assigned to the modulation scheme.

20. A computer program encoded on a nontransient memory and which is executable on a computer appliance that interacts with the sensor system as claimed in claim 1 that is configured to carry out spectral analysis of a signal recorded by a camera of a mobile computer appliance connected to the sensor system.

21. A method for producing a sensor system as claimed in claim 1, wherein a structure of the sensor system is thermally formed in a thermoplastic polymer by an upper die and a lower die between which the thermoplastic polymer is pressed.

* * * * *